(12) United States Patent
Rando

(10) Patent No.: US 7,244,712 B2
(45) Date of Patent: Jul. 17, 2007

(54) AMINOGLYCOSIDE ANTIBIOTICS AND METHODS OF USING SAME

(75) Inventor: Robert R. Rando, Newton Centre, MA (US)

(73) Assignee: President and Fellows of Harvard College, Cambridge, MA (US)

(*) Notice: Subject to any disclaimer, the term of this patent is extended or adjusted under 35 U.S.C. 154(b) by 183 days.

(21) Appl. No.: 10/941,623

(22) Filed: Sep. 14, 2004

(65) Prior Publication Data
US 2005/0090462 A1 Apr. 28, 2005

(51) Int. Cl.
*A61K 31/704* (2006.01)
*C07H 15/00* (2006.01)

(52) U.S. Cl. ............... 514/35; 514/36; 514/39; 514/41; 514/25; 536/16.8; 536/17.2; 536/17.5; 536/17.9; 536/13.2; 536/23.1; 536/16.6; 536/24.1; 435/6; 435/69.1; 435/194; 435/69.3

(58) Field of Classification Search ............... 536/16, 536/8, 17.2, 17.5, 17.6, 17.9, 16.8, 13.2, 536/23.1, 16.6, 24.1; 514/25, 35, 36, 41, 514/39; 435/6, 69.1, 194, 252.3, 5, 69.3
See application file for complete search history.

(56) References Cited
U.S. PATENT DOCUMENTS

| | | | |
|---|---|---|---|
| 4,008,362 A | 2/1977 | Akita et al. | |
| 4,065,616 A | 12/1977 | Umezawa et al. | |
| 4,252,970 A | 2/1981 | Magerlein | |
| 4,281,107 A | 7/1981 | Suami | |
| 6,482,802 B1 | 11/2002 | Hu et al. | |

OTHER PUBLICATIONS

Wang et al. "Specificity of aminoglycoside binding to RNA constructs derives from the 16S rRNA decoding region and the HIV-RRE activator region." Biochemistry, 36, 768-779, 1997.*

* cited by examiner

*Primary Examiner*—Shaojia Anna Jiang
*Assistant Examiner*—Devesh Khare
(74) *Attorney, Agent, or Firm*—Edwards Angell Palmer & Dodge LLP; George W. Neuner; Dwight D. Kim

(57) ABSTRACT

The present invention relates to aminoglycoside compounds having antibiotic activity. Moreover, the present invention relates to L-aminoglycoside compounds and diastereomers thereof which posses antibiotic activity and are not susceptible to development of resistant bacterial strains. The present invention also relates to methods of treatment and pharmaceutical compositions that utilize or comprise one or more of aminoglycoside compounds provided by the invention.

11 Claims, 14 Drawing Sheets

```
                                               G-C
                                               G-C
                                               C-G
                                               U-A
    5' 3'              5' 3'                   UoG
    G-C                G-C                     A-U
    G-C                G-C                     G-C
    C-G                C-G                  A UoG
    G-C                G-C                U
    UoU                UoU                   A GoU
    C-G                C-G                    C-G
    A-A                G-A                    G-C
      A                  A                    A-U
    C-G                C A                    G-C
    A-U                U-A                    G-C  A
    C-G                A-U                    U-A
    C-G                C-G                   U   U
    U  G               U  G                  U   C
    UC                 UC                     A G

Neomycin B: 0   12.5   25   50 μM

D-neamine: 0   25   50   100 μM

L-neamine: 0   100   200   500 μM

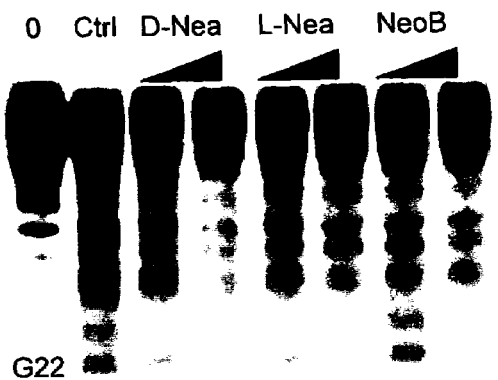
FIG. 13A  FIG. 13B

US 7,244,712 B2

AMINOGLYCOSIDE ANTIBIOTICS AND METHODS OF USING SAME

STATEMENT REGARDING FEDERALLY-SPONSORED RESEARCH

This invention was made with government support under Grant EY-12375 from the U.S. Public Health Service, NIH. The government has certain rights in the invention.

CROSS-REFERENCE TO RELATED APPLICATION(S)

This application claims the benefit of PCT Application Ser. No. PCT/US03/07930 filed Mar. 14, 2003, U.S. Provisional Application Ser. No. 60/364,340 filed Mar. 14, 2002 and of U.S. Provisional Application Ser. No. 60/394,763 filed Jul. 10, 2002, the teachings of which are incorporated herein by reference.

FIELD OF THE INVENTION

The present invention relates to a new class of compounds which are capable of inhibiting bacterial growth. More particularly, the invention provides a new class of L-aminoglycoside compounds which inhibit bacterial growth including the inhibition of growth of bacterial strains which are resistant to D-aminoglycoside compounds. The present invention also relates to methods of inhibiting bacterial growth and methods of administering compounds of the invention to patients suffering from or susceptible to a bacterial infection.

BACKGROUND OF THE INVENTION

RNA molecules are targets for small molecule drugs. In fact, several clinically useful drugs operate by interfering with RNA function. Perhaps the most noteworthy examples are found among the antibiotics, and here the most useful RNA binding drugs are the aminoglycosides (Gale, E. F., Cundliffe, E., Reynolds, P. E., Richmond, M. H., & Waring M. J. (1981) The Molecular Basis of Antibiotic Action, 2$^{nd}$ ed., John Wiley & Sons, London, Great Britain, pp 419-439; Cundliffe, E. (1989) Annu. Rev. Microbiol. 43, 207-233). Aminoglycoside antibiotics function by binding to the A-site decoding region on bacterial 16S ribosomal (r)RNA (Scheme 1/fig9) (Noller, H. F. (1991) Annu. Rev. Biochem. 60, 191-227; Woodcock, J., Moazed, D., Cannon, M., Davies, J. and Noller, H. F. (1991) EMBO J. 10, 3099-3103). This binding alters the interactions between the codon-anticodon helix and the A-site RNA, causing mis-translation, and premature termination during protein synthesis in bacteria. This leads to the bactericidal effects of this class of drugs (Cundliffe, E. (1990) The Ribosome: Structure, Function & Evolution (Hill, W. E., Dahlberg, A. E., Garret, R. A., Moore, P. B., Schlessinger, D., & Warner, J. R., Eds.), American Society for Microbiology, Washington, D.C., pp 479-490; Chambers, H. F., & Sande, M. A. (1996) Goodman & Gilman's The Pharmacological Basis of Therapeutics (Hardman, J. G., Limbird, L. E., Molinoff, P. B., Ruddon, R. W., & Gilman, A. G., Eds.) 9$^{th}$ ed., McGraw-Hill, New York. Chap. 46, pp 1103-1121). An essential question to address with aminoglycosides is how specific are their interactions with targets, and to what structural elements do they owe their specificity of action.

Aminoglycosides have been found to bind to many different types of RNA structures (Zapp, M. L., Stern, S., & Green, M. R. (1993) Cell 74, 969-978; Werstuck, G., Zapp., M. L., & Green, M. R. (1996) Chem. Biol. 3, 129-137; Mei, H. Y., Cui, M., Heldsinger, A., Lemrow, S. M., Loo, J. A., Sannes-Lowery, K. A., Sharmeen, L., and Czarnik, A. W. (1998) Biochemistry 37, 14204-14212; Tok, J. B., Cho, J., & Robert, R. R. (1999) Biochemistry 38, 199-206; Stage, T. K., Hertel. K. J., & Uhlenbeck, O. C. (1995) RNA 1, 95-101). In addition to their pharmacologically relevant A-site decoding region targets (Scheme 1/fig9), aminoglycosides have been found to bind to regions of HIV mRNA, to thymidylate synthase mRNA, and to a variety of RNA molecules selected to bind to aminoglycosides (Wang, Y., & Rando, R. R. (1995) Chem. Biol. 2, 281-290; Lato, S. M., Boles, A. R., & Ellington, A. D. (1995) Chem. Biol. 2, 291-303; Wallis, M. G., Von Asen, U., Schroeder, R., & Famulok, M. (1995) Chem. Biol. 2, 543-552). Save for one notable instance, in which nM binding is found (Cho, J., Hamasaki, K., and Rando, R. R. (1998) Biochemistry 37, 4985-4992;Hamasaki, K., Killian, J. Cho, J., and Rando, R. R. (1998) Biochemistry 37, 656-663), typical binding affinities in the μM range are found for the interactions of aminoglycosides and RNA molecules. RNA molecules that bind to aminoglycosides typically possess non-duplex structural elements (Cho, J. and Rando, R. R. (1999) Biochemistry 38, 8548-8554). Often these RNA molecules contain asymmetric bulges or bubbles, which allow aminoglycoside access to the purine and pyrimidine bases.

Previous binding experiments on prokaryotic A-site decoding region RNA constructs measured affinities for D-aminoglycosides in the 1-2 μM range, save for neomycin B, which had a somewhat higher affinity. Similar observations were also made in studies on the binding of D-aminoglycosides to human decoding region A-site constructs. Binding studies have established that a wide variety of structurally dissimilar D-aminoglycosides have similar affinities for RNA substrates. See, for example, Ryu, D. H. and Rando, R. R. Bioorganic and Medicinal Chemistry, (In Press); and Wang, Y., Hamasaki, K., & Rando, R. R. (1997) Biochemistry 36, 768-77.

A structurally diverse family of D-aminoglycosides are known to be effective antibiotics (Chambers, H. F., & Sande, M. A. (1996) Goodman & Gilman's The Pharmacological Basis of Therapeutics (Hardman, J. G., Limbird, L. E., Molinoff, P. B., Ruddon, R. W., & Gilman, A. G., Eds.) 9 th ed., McGraw-Hill, New York. Chap. 46, pp 1103-1121).

The ready development of resistant strains of various organisms to aminoglycoside compounds limits the application of these compounds as antibacterial agents. Bacteria, protozoa and other single cell organisms have a number of deactivation pathways available which can render an amindoglycoside inactive. For example, bacteria have a number of enzymes which are capable of metabolizing an aminoglycolide into non-cytotoxic species such as by phosphorylation, saccharide bio-degradation and the like. The ability of bacterium and other single cell organisms to quickly develop resistance to aminoglycosides limits current antibiotic applications.

It would be desirable to design new aminoglycolide compounds which inhibit bacteria growth, e.g., possess anti-bacterial activity, and are not susceptible to formation of resistant cellular strains.

SUMMARY OF THE INVENTION

The present invention provides new aminoglycoside compounds that inhibit bacteria growth, preferably compounds that inhibit growth of bacteria resistant to current aminoglycoside antibiotics. The invention further includes methods of inhibiting bacteria growth and methods of administering an aminoglycoside compound of the invention to a patient suffering from or susceptible to a bacterial infection.

The present invention provides a new class of aminoglycoside antibiotics comprising one or more non-natural saccharide residues. Preferred aminoglycoside compounds of the invention comprise at least two non-natural saccharide residues such as an L-neamine structure preferrably having one or more additional natural or non-natural saccharide residues coupled to the L-neamine core. Particularly preferred aminoglycosides of the invention are mirror images of known aminoglycosides antagonists, e.g., non-naturally occurring enantiomers of known D-aminoglycoside compounds having antibiotic activity.

The present invention also provides methods of inhibiting bacterial growth using an aminoglycoside compound comprising at least on L-saccharide residue and preferably using an aminoglycoside that is a mirror image of a known D-aminoglycoside antagonist.

The present invention further provides methods of administering a compound of the invention to a patient who is suffering from or susceptible to an infection, particularly an infection of bacteria, protozoa, yeast or the like.

Definitions

The instant invention is most clearly understood with reference to the following definitions:
rRNA, ribosomal RNA;
HIV, human Immunodeficiency virus;
mRNA, messenger RNA;
CRP, 5-carboxytetramethyl rhodamine-labeled paromomycin;
CRT, 5-carboxytetramethyl rhodamine-labeled tobramycin;
CD, circular dichroism;
CPG, controlled pore glass;
HEPES, 4-(2-hydroxyethyl)piperazine-1-sulfonic acid;
DTT, dithio threitol;
OD, optical density;
EDTA, ethylenediamine tetraacetic acid;
ATCC, American Type Culture Collection;
APH, aminoglycoside phosphotransferase;
NPT, neomycin phosphotransferase;
WT, wild type;
MIC, minimal inhibitory concentration;
$K_D$, $K_d$, dissociation constants;
NMR, nuclear magnetic resonance.
MOM, methoxymethyl.
RNA Aptamer, A single stranded RNA molecule that binds to specific molecular targets such as a protein or metabolite.

BRIEF DESCRIPTION OF THE DRAWINGS

For a fuller understanding of the nature and desired objects of the present invention, reference is made to the following detailed description taken in conjunction with the accompanying figures wherein:

FIG. 9 is an image of the Bacterial (B), Human (H) A-Site Decoding Region Constructs and the Tobramycin Binding Aptamer Construct (J6f1);

FIG. 11 is an image of the Bacterial A-Site Decoding Region L-RNA Construct with (D-A)$_3$;

FIG. 13A is a gel-electrophoresis of footprinting studies of aminoglycoside binding to D-A-site RNA constructs. 0, untreated A-site RNA ($^{32}$P-labeled at 5' end); Ctrl, control experiment in the absence of binders; D-Nea, L-Nea, NeoB-RNA footprinting in the presence of D-neamine, L-neamine and neomycin B; Concentrations of the aminoglycosides: 50 and 250 μM.

FIG. 13B is a gel-electrophoresis of footprinting studies of aminoglycoside binding to L-A-site RNA constructs. 0, untreated A-site RNA ($^{32}$P-labeled at 5' end); Ctrl, control experiment in the absence of binders; D-Nea, L-Nea, NeoB-RNA footprinting in the presence of D-neamine, L-neamine and neomycin B; Concentrations of the aminoglycosides: 50 and 250 μM.

DETAILED DESCRIPTION OF THE INVENTION

Figure 1A:
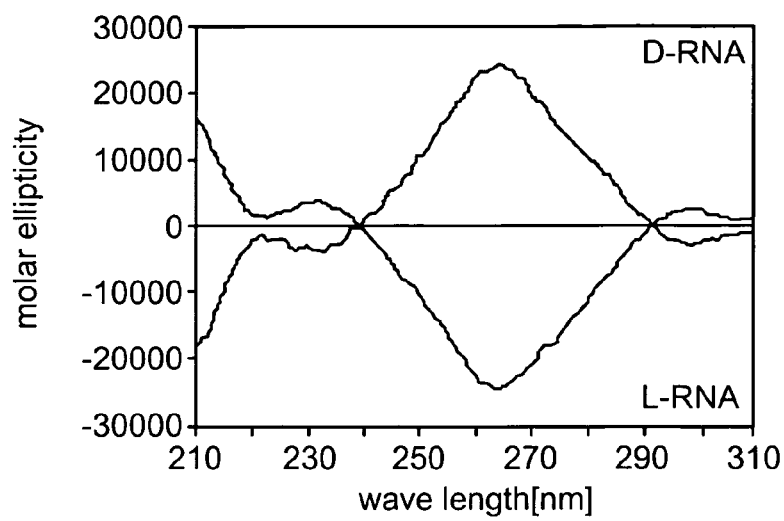
FIG. 1A is a circular dichroism (CD) spectra of L-RNA construct B performed by mixing 50 mL stock solution+450 mL 100 mM sodium chloride, 10 mM sodium hydrogen phosphate pH 7.0 at 4° C. on an Aviv 202 spectropolarimeter.

The present invention provides aminoglycoside compounds comprising at least one saccharide residue having at least one sugar hydroxyl residue is replaced with an amino residue. Such amino functionalized sugars are interchangeably referred to as azasugars, aza-saccharides or aminoglycosides. Preferred aminoglycosides of the invention include diastereomers or enantiomers of D-neamine, a common aminoglycoside structural unit, or a derivative thereof. Preferred aminoglycoside compounds include those aminoglycoside compounds wherein substantially all of the azasugar residues of the aminoglycoside compound are L-azasugar residues which are diastereomers or enantiomers of D-neamine or a derivative thereof.

Preferred embodiments of the invention provides L-aminoglycoside compounds which are enantiotopic, mirror images of naturally occurring or synthetic D-aminoglycoside compounds possessing anti-bacterial properties. Other aminoglycoside compounds provided by the invention include diastereotopic aminoglycoside compounds which differ from preferred L-aminoglycoside compounds of the invention by the stereochemical identity of one or more stereogenic centers. In general, the present invention provides L-aminoglycoside compounds which are exact mirror images of naturally occurring or synthetic D-aminoglycosides and diastereomers of the mirror-image L-aminoglycosides (L-aminoglycoside diasteromers) of the invention which have opposite stereochemical identity at one or more stereocenters. Preferred L-aminoglycoside diasteromers of the invention include those diasteromers which differ from the mirror image L-aminoglycoside by the stereochemistry at one, two or three stereogenic centers.

Preferred aminoglycoside compounds of the invention include, e.g., L-neamine, L-neamine diasteromers differing from L-neamine in the stereochemical identity of between 1 and 3 stereocenters, and aminoglycosides having a L-neamine or L-neamine diasteromer coupled to one or more D- or L-sugar or D- or L-azasugar residues. Preferred aminoglycosides of the invention may be optionally substituted at one or more hydroxyl or amino functional groups.

Particularly preferred L-aminoglycoside compounds include L-neamine or a L-neamine derivative selected from the group consisting of L-neomycin, L-paromomycin, L-kanamycin, and L-tobramycin.

Aminoglycoside compounds provided in the present invention including L-neamine, L-neamine derivatives and diastereomers of L-neamine and L-neamine derivatives are capable of inhibiting bacterial growth. Particularly preferred aminoglycoside compounds of the invention include those L-aminoglycoside compounds which possess antibiotic activity against strains of bacteria or yeast which are resistant to the enantiotopic D-aminoglycoside compounds. Certain preferred L-aminoglycoside compounds of the invention are not susceptible to enzymatic degradation processes.

Preferred compounds provided by the present invention include those compounds according to Formula I:

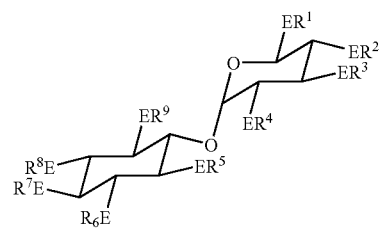

wherein

E is independently selected at each occurrence of E in the formula from the group consisting of O, NH, and N-C$_{1-6}$alkyl, such that at least one occurrence of E is not oxygen; and R$^1$, R$^2$, R$^3$, R$^4$, R$^5$, R$^6$, R$^7$, R$^8$, and R$^9$ are independently selected at each occurrence from the groups consisting of hydrogen, C$_{1-6}$alkyl, C$_{1-6}$alkanoyl, monosaccharides, disaccharides, mono-azasaccharides, and di-azasaccharides, where each saccharide or azasaccharide residue is either a D-saccharide or an L-saccharide.

Particularly preferred compounds of the invention include compounds according to Formula II:

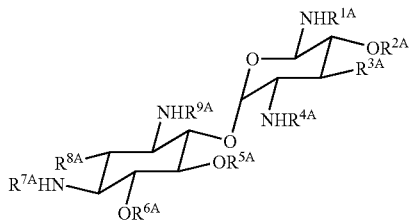

wherein $R^{1A}$, $R^{2A}$, $R^{4A}$, $R^{5A}$, $R^{6A}$, $R^{7A}$, and $R^{9A}$ are independently selected at each occurrence from the groups consisting of hydrogen, alkyl, alkanoyl, monosaccharides, disaccharides, mono-azasaccharides, and di-azasaccharides, where each saccharide or azasaccharide residue is either a D-saccharide or an L-saccharide; and $R^{3A}$ and $R^{8A}$ are independently selected at each occurrence from the groups consisting of hydrogen, hydroxy, amino, $C_{1-6}$alkoxy, amino, mono and di$C_{1-6}$alkylamino, carboxamide, monosaccharides, disaccharides, mono-azasaccharides, and di-azasaccharides, where each saccharide or azasaccharide residue is either a D-saccharide or an L-saccharide.

In other embodiments of the present invention, pharmaceutical compositions are provided which comprise an aminoglycoside compound of the invention, preferably an L-aminoglycoside according to either Formula I or II, and a pharmaceutically acceptable carrier.

The present invention also provides methods of inhibiting growth of a bacteria or yeast comprising the steps of providing an aminoglycoside compound of Formula I or II;

contacting the L-aminoglycoside compound with the bacteria or yeast under conditions conducive to the inhibition of growth.

Preferred methods of inhibiting growth of a bacterial or yeast include the use of an aminoglycoside selected from those aminoglycosides having at least one azasugar residue which is a diasteroemer or enantiomer of D-neamine or a derivative thereof.

Preferred L-aminoglycoside compounds of the invention are capable of binding to one or more RNA sequences. Typically, binding affinity is measured by a dissociation constant which quantifies the binding efficiency with which a compound binds to one or more RNA sequences. In general, tightly associated RNA-compound complex have small dissociation constants. Particularly preferred L-aminoglycoside compounds have a RNA dissociation constant of less than about 100 μM, typically the dissociation constant is between about 0.01 μM and about 100 μM. More preferably, the dissociation constant is less than about 100 μM, 75 μM, 50 μM, 25 μM, 10 μM, 5 μM, or 1 μM. Particularly preferred aminoglycoside compound comprising at least one azasugar residue, e.g., a sugar residue in which one or more hydroxyl groups are replaced with amino groups, which is a diasteroemer or enantiomer of D-neamine or a derivative thereof have a RNA dissociation constant of between about 0.1 μM and about 20 μM.

Preferred L-aminoglycoside compounds of the invention are capable of inhibiting bacterial growth. Typically, antibiotic activity is measured using a standard disk assay using sterile paper disks soaked with various concentrations of solutions of compounds of the invention. In general, minimal inhibitory concentrations (MIC) were measured using the technique published by Greenberg et al. in *J. Am. Chem. Soc.* 1999, 121:6527-6541. Particularly preferred L-aminoglycoside compounds have a MIC of less than about 5000 μM, typically the MIC is less than about 4000 μM, 3000 μM, 2500 μM, 2000 μM, 1500 μM, or 1000 μM. Particularly preferred aminoglycoside compound comprising at least one azasugar residue, e.g., a sugar residue in which one or more hydroxyl groups are replaced with amino groups, which is a diasteroemer or enantiomer of D-neamine or a derivative thereof have a minimal inhibitory concentration of less than about 2000 μM.

The present invention also provides methods for treating a mammal suffering or susceptible to a bacterial or yeast infection or disorder, comprising administering to the mammal an effective amount of an aminoglycoside compound comprising at least one azasugar residue which is a diasteroemer or enantiomer of D-neamine or a derivative thereof. Preferably, aminoglycoside compounds are administered to a mammal already suffering from a bacterial or yeast infection. Preferred mammals include humans and domesticated animals such as dogs, cats, pigs, bovine, sheep and the like. Humans are a particularly preferred mammal for administration of an aminoglycoside compound of the present invention.

The aminoglycoside compounds of the present invention are suitable for treatment of any bacterial or yeast infection. Examples of bacterial infections and yeast infections, which are suitable for treatment by administration of an aminoglycoside compound of the invention, include various bacteria and yeast strains associated with inducing illnesses and diseases.

For such treatment, the compounds of the invention are administered in effective amounts and in appropriate dosage form ultimately at the discretion of the medical or veterinary practitioner. For example, as known to those skilled in the art, the amount of compounds of the invention required to be pharmaceutically effective will vary with a number of factors such as the mammal's weight, age and general health, the efficacy of the particular compound and formulation, route of administration, nature and extent of the condition being treated, and the effect desired. The total daily dose may be given as a single dose, multiple doses, or intravenously for a selected period. Efficacy and suitable dosage of a particular compound can be determined by known methods. More particularly, for treatment of a tumor in a mammal such as a human, particularly when using more potent compounds of the invention, a typical effective dose of the compound of the invention will be in the range of 0.1 to 100 milligrams per kilogram body weight of recipient per day, preferably in the range of 1 to 10 milligrams per kilogram body weight of recipient per day. The desired dose is suitably administered once daily, or as several sub-doses, e.g. 2 to 4 sub-doses administered at appropriate intervals through the day, or other appropriate schedule. Such sub-doses may be administered as unit dosage forms, e.g., containing from 0.2 to 200 milligrams of compound(s) of the invention per unit dosage, preferably from 2 to 20 milligrams per unit dosage.

Naturally, the formulation and typical dosage of a compound of the invention will vary depending on the mode of administration, e.g., oral or topical administration may require a higher or lower dosage than administration by injection.

The compounds of the present invention may be suitably administered to a subject as a pharmaceutically acceptable salt. Such salts can be prepared in a number of ways. For example, where the compound comprises a basic group such as an amino group, salts can be formed from an organic or inorganic acid, e.g. hydrochloride, sulfate, hemisulfate, phosphate, nitrate, acetate, oxalate, citrate, maleate, etc.

The therapeutic compound(s) may be administered alone, or as part of a pharmaceutical composition, comprising at least one compound of the invention together with one or more acceptable carriers thereof and optionally other therapeutic ingredients. The carrier(s) must be "acceptable" in the sense of being compatible with the other ingredients of the formulation and not deleterious to the recipient thereof.

The compositions include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well known in the art of pharmacy.

Such methods include the step of bringing into association the to be administered ingredients with the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for oral administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for topical administration to the skin may be presented as ointments, creams, gels and pastes comprising one or more compounds of the present invention and a pharmaceutically acceptable carrier. A suitable topical delivery system is a transdermal patch containing the ingredient to be administered.

Compositions suitable for rectal administration may be presented as a suppository with a suitable base comprising, for example, cocoa butter or a salicylate.

Compositions suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above the formulations of this invention may include other agents conventional in the art having regard to the type of formulation in question, for example, those suitable for oral administration may include flavoring agents.

In particularly preferred embodiments of the present invention, aminoglycoside compounds comprising a neamine residue are provided such as L-neamine, ent-1, positional isomers of D-neamine, 2 and 3, and positional isomers of L-neamine, ent-2 and ent-3 (Table 1).

TABLE 1

Structures of 2-deoxystreptamine, natural D-neamine (1), L-neamine (ent-1) and their positional isomers (2, 3, ent-2 and ent-3).

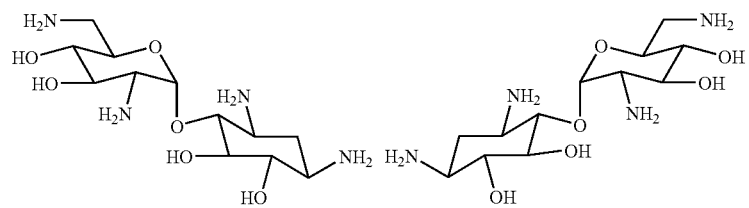

TABLE 1-continued
Structures of 2-deoxystreptamine, natural D-neamine (1), L-neamine (ent-1) and their positional isomers (2, 3, ent-2 and ent-3).
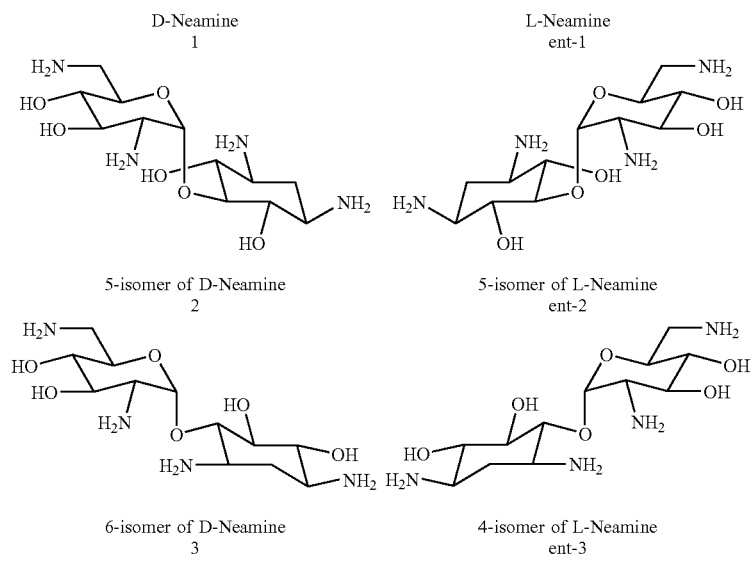
Other preferred compounds of the present invention include L-neamine and L-enantiomers of the D-aminoglycoside derivatives of D-neamine which possess antibiotic activity such as D-neomycin, D-paromomycin, D-kanamycin B, and D-tobramycin.
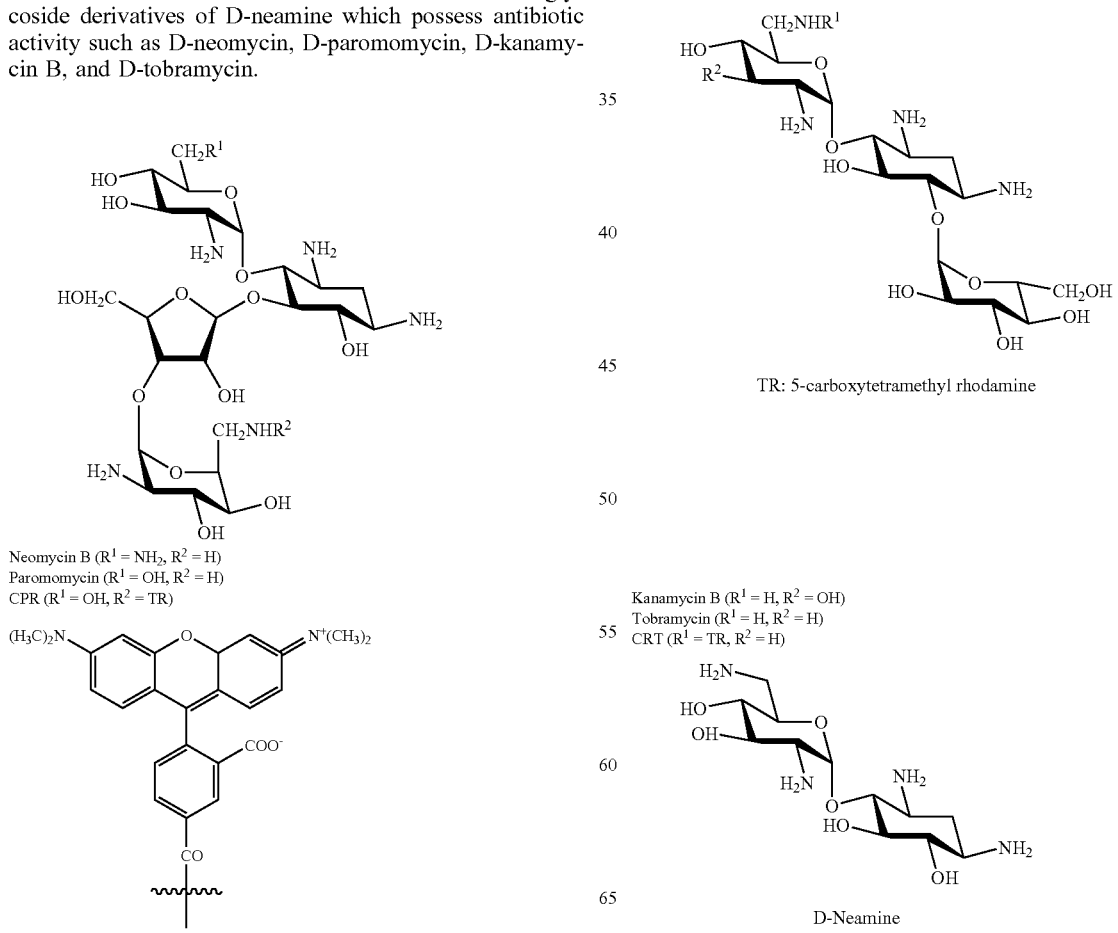

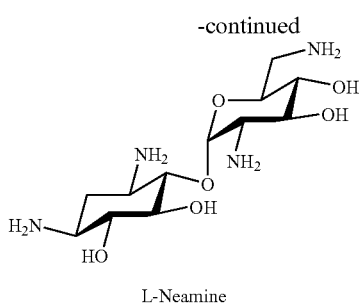

L-Neamine

Aminoglycoside antibiotics function by binding to the A-site decoding region of bacterial rRNA causing mistranslation and/or premature message termination. Given the broad range of aminoglycoside structural types that can act as anti-bacterial drugs it seems unlikely that aminoglycosides bind in a unique way to their functional target. One way to gauge specificity of drug-target interactions is to probe the stereospecificity of the interactions. A-site decoding region rRNA constructs bind a series of aminoglycosides in a non-stereospecific manner with dissociation constants in the 1-5 µM range. Synthetic D and L-neamine were prepared and found also to bind to both bacterial and yeast ribosomes with similar affinities. Finally, unnatural L-neamine, like D-neamine, inhibits the growth of E. coli and P. aerugenosa. Moreover, L-neamine also inhibits the growth of aminoglycoside resistant E. coli which expresses a kinase that detoxifies aminoglycosides of the D-series, suggesting that mirror image aminoglycosides may avoid certain forms of enzyme-mediated resistance.

NMR investigations on the binding of aminoglycosides to the truncated A-site decoding region construct B suggests elements of specificity in the binding (Fourmy, D., Recht, M. I., Blanchard, S. C., & Puglisi, J. D. (1996) Science 274, 1367-1371; and Lynch, S. R. & Puglisi, J. D. (2001) J. Mol. Biol. 306, 1037-1058.). In addition, recent structural studies on ribosomal subunits demonstrate specificity in A-site interactions with mRNA and tRNA codon-anticodon complexes as well as with aminoglycosides. For example, the aminoglycoside paromomycin distorts decoding region interactions facilitating the binding of near cognate tRNAs. See, for example, Wimberly, B. T., Brodersen, D. E., Clemons, W. M., Jr., Morgan-Warren, R. J., Carter, A. P., Vbnrhein, C., Hartsch, T., & Ramakrishnan, V. (2000) Nature 407, 327-339; Carter, A. P., Clemons, W. M., Brodersen, D. E., Morgan-Warren, R. J., Wimberly, B. T., & Ramakrishnan, V. (2000) Nature 407, 340-348; Ogle, J. M., Brodersen, D. E., Clemons, W. M., Jr., Tarry, M. J., Carter, A. P., & Ramaloridhnan, V. (2001) Science 292, 897-902; and Yusupov, M. M., Yusupova, G. Z., Baucom, A., Lieberman, K., Earnest, T. N., Cate, J. H., & Noller, H. F. (2001) Science 292, 883-896.

Because aminoglycosides are arguably the most clinically important group of drugs known to target RNA molecules, it is important to establish the order of selectivity of this class of drugs. Applicants have surprisingly discovered that a diverse structural family of aminoglycosides bind to similar common RNA decoding target region in a non-stereospecific manner. Moreover, structurally diverse aminoglycosides bind to a broad collection of RNA molecules with similar affinities. See, for example, the structurally diverse eukaryotic and prokaryotic decoding region constructs presented in FIG. 9A-C bind with several D-aminoglycosides with about the same affinity.

We have found that aminoglycoside-target interactions are non-stereospecific. It is generally accepted that aminoglycosides can bind to a myriad of RNA structures that contain non-duplex regions. An important question to address is how specifically aminoglycosides bind to their pharmacological targets, namely the A-site rRNA decoding regions of susceptible bacteria.

D-aminoglycosides bind to both natural RNA substrates and unnatural RNA substrates. In a non-limiting example, the D-enantiomer and the L-enantiomer of prokaryotic A-site RNA constructs (denoted hereinafter and in the figures as "B"), have been prepared and the ability of D-aminoglycosides to bind to each RNA enantiomer determined. The D-aminoglycloside compounds bind to the naturally occurring RNA sequences and mirror image enantiomer thereof establishing that non-stereospecific binding behavior for aminoglycosides for RNA. Moreover, D-aminoglycoside compounds bind to both D-RNA and L-RNA constructs. L-aminoglycoside compounds also bind to both D-RNA and L-RNA constructs. Typically, binding of D-aminoglycosides to D-series RNA sequences ('naturally occurring' RNA) occurs with greater affinity than binding to the 'unnatural' L-RNA sequence, e.g., $K_d$ (natural)<$K_d$ (unnatural).

Non-sterospecific binding is also observed in the human (denoted hereinafter and in the figures as "H") decoding region constructs such that the difference in binding affinity of D-aminoglycosides for binding to the natural and non-natural enantiomers of the decoding region is negligible.

Typically, the naturally occurring aminoglycosides exhibited a modest 2-3 fold increase in selectivity for the D-series RNA construct. In the case of kanamycin, binding to the unnatural L-RNA was favored by a factor of approximately 1.5 over the D-decoding region construct. The general drift towards enhanced binding of the cognate RNA construct was also observed in the case of D and L-neamine. Both enantiomers were preferentially bound to their stereochemical cognate by a factor of approximately two-fold relative to the enantiomers.

Experiments were designed to probe the stereospecificity of aminoglycoside binding to the RNA constructs shown in FIG. 9 because these small rRNA constructs mimic ribosomal decoding region RNA function. The three constructs shown include a bacterial 16S A-site rRNA construct (B) (27), its human counterpart (H), and an RNA aptamer (J6f1) selected to bind to the aminoglycoside tobramycin (12,15, 16).

Figure 1B:
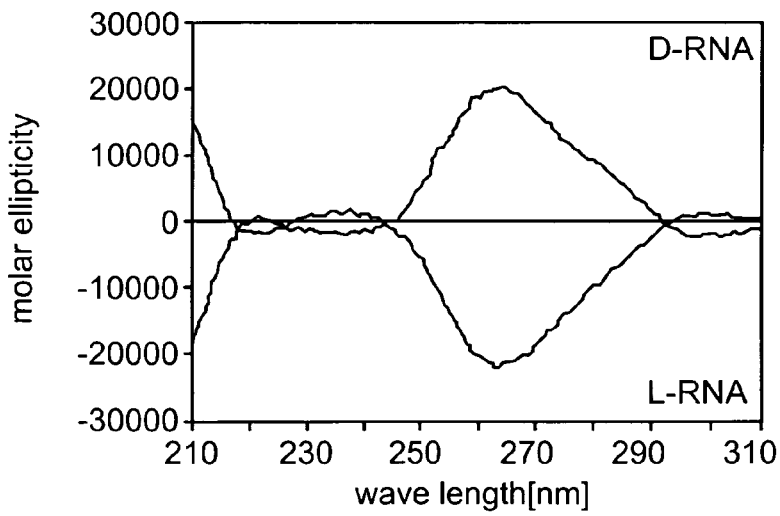
FIG. 1B is a circular dichroism (CD) spectra of L-RNA construct H performed by mixing 50 mL stock solution+450 mL 100 mM sodium chloride, 10 mM sodium hydrogen phosphate pH 7.0 at 4° C. on an Aviv 202 spectropolarimeter.
Figure 1C:
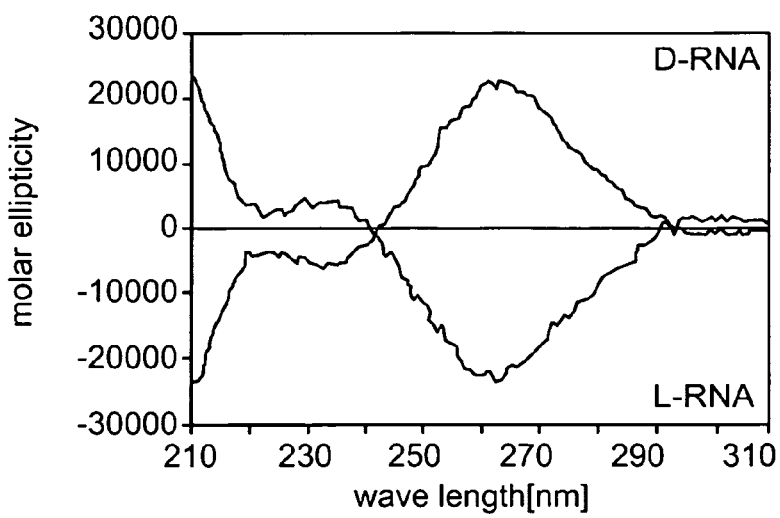
FIG. 1C is a circular dichroism (CD) spectra of L-RNA construct J6f1 performed by mixing 50 mL stock solution+450 mL 100 mM sodium chloride, 10 mM sodium hydrogen phosphate pH 7.0 at 4° C. on an Aviv 202 spectropolarimeter.

Aminoglycoside binding to RNA construct, J6f1, (FIG. 9C) is of interest because of the high-level of binding specificity this construct exhibits for D-aminoglycoside compounds such that RNA construct, J6f1, (FIG. 9C) is a useful as a control for studying binding of aminoglycosides with RNA decoding region constructs. L-aminoglycoside binding to D-RNA sequences are energetically equivalent to binding the enantiotopic D-aminoglycoside to an L-RNA sequence. Initial binding experiments were carried out using enantiomerically pure L-RNA constructs, B, H, and J6f1 (FIG. 9A-C) and D-aminoglycoside compounds. Circular dichroism spectra of the purified constructs confirm the enantiomeric relationship of the corresponding D-RNA and L-RNA constructs (FIGS. 1A-C). The constructs were tested for aminoglycoside binding using the fluorescence anisotropy method described in Example 4. In these measurements, the fluorescent aminoglycoside CRP bearing a rhodamine chromaphore is used to monitor binding to the decoding region constructs (B and H) and fluorescent aminoglycoside CRT bearing a rhodamine chromaphore was used to monitor binding to RNA construct J6f1 (FIG. 9C).

See, for example, Wang, Y. and Rando, R. R. *Chem. Biol.* (1995) 2, 281-290; Hamasaki, K., Killian, J. Cho, J., and Rando, R. R. *Biochemistry* (1998) 37, 656-663; and Cho, J. and Rando, R. R. (1999) Biochemistry 38, 8548-8554.

Figure 2A:
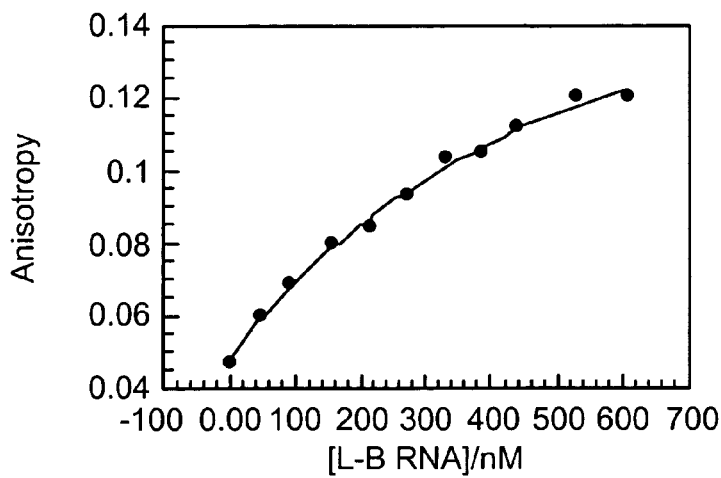
FIG. 2A is a plot of fluorescence anisotropy of fluorescently labeled paromomycin (CRP) (20 nM) as a function of L-RNA construct B concentration.
Figure 2B:
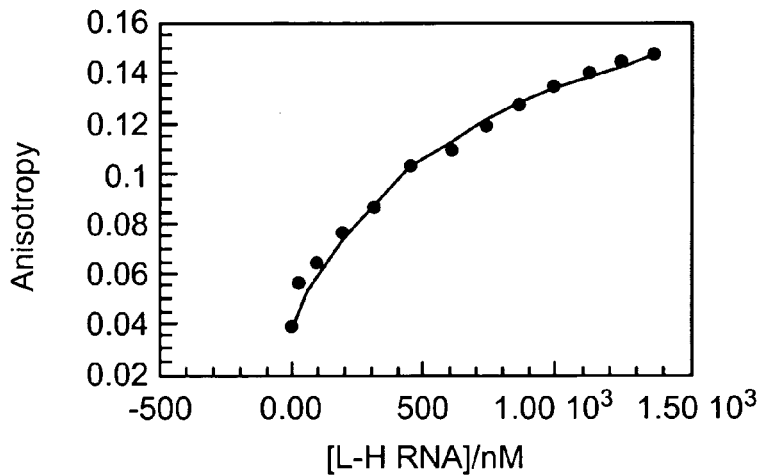
FIG. 2B is a plot of fluorescence anisotropy of fluorescently labeled paromomycin (CRP) (20 nM) as a function of L-RNA construct H concentration.
Figure 2C:
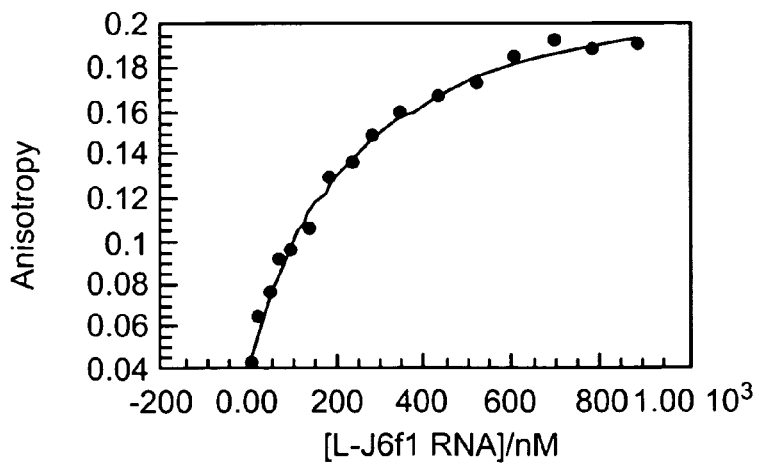
FIG. 2C is a plot of fluorescence anisotropy of fluorescently labeled tobramycin (CRT) (20 nM) as a function of L-RNA construct J6f1 concentration.
Figure 3A:
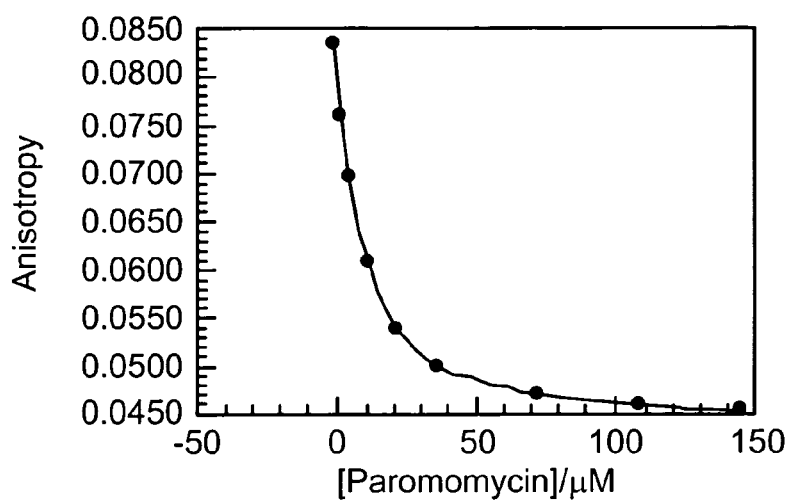
FIG. 3A is a plot of fluorescence anisotropy of fluorescently labeled paromomycin (CRP) (20 nM) containing L-RNA construct B as a function of paromomycin concentration.
Figure 3B:
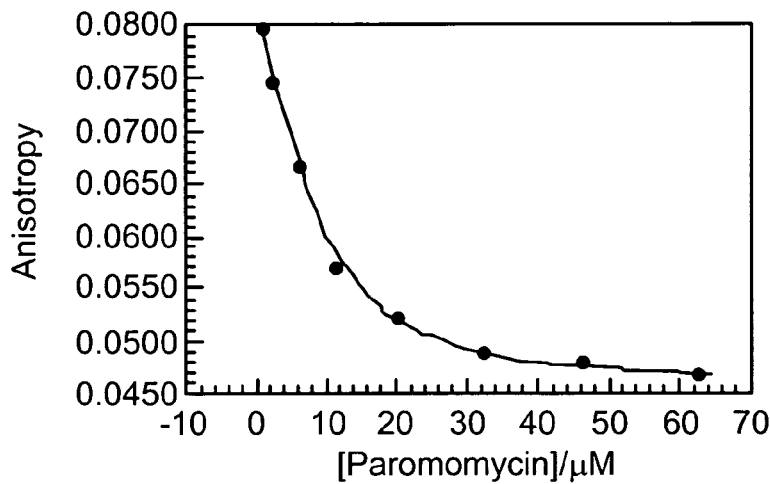
FIG. 3B is a plot of fluorescence anisotropy of fluorescently labeled paromomycin (CRP) (20 nM) containing L-RNA construct H as a function of paromomycin concentration.
Figure 3C:
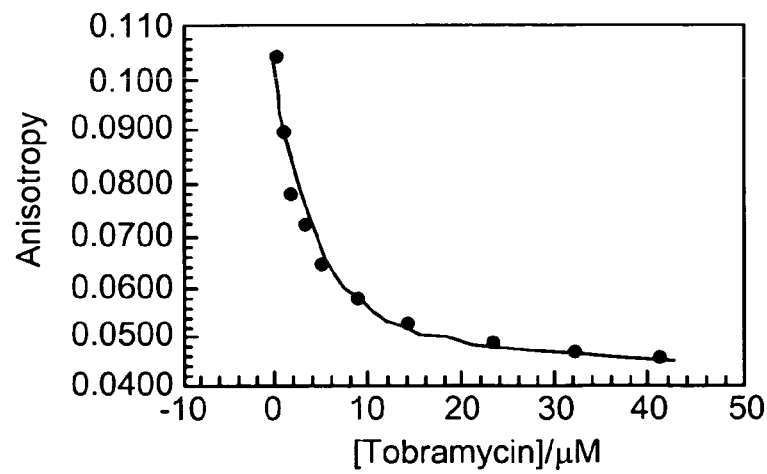
FIG. 3C is a plot of fluorescence anisotropy of fluorescently labeled tobramycin (CRT) (20 nM) containing L-RNA construct J6f1 as a function of tobramycin concentration.

The binding data, shown in FIG. 2A-C, for the L-RNA constructs demonstrates non-stereospecificity of aminoglycoside binding to RNA. Competition experiments provide further evidence for non-stereospecific binding. In an illustrative example, competition experiments using paromomycin for the decoding regions B and H (FIGS. 9A and 9B) and tobramycin for decoding region RNA construct, D-J6f1, (FIG. 9C) are shown in FIG. 3A-C. Table 2 provides binding data for the various D-aminoglycosides for complexation with the D-RNA and L-RNA enantiomers of decoding region constructs B and H and complexation with the D- and L-enantiomers of J6f1. These data indicate that aminoglycoside binding to the prokaryotic decoding region A-site construct is weakly stereospecific. In contrast, aminoglycoside binding to the aptamer J6f1 is strongly stereospecific. The measured affinities for the D-decoding region construct is consistent with results of binding measurements on prokaryotic ribosomes using radioactive tobramycin (Le Goffic, F., Capmau, M.-L., Tangy, F. and Baillarge, M. (1979) *Eur. J. Biochem.* 102,73-81). Binding affinities in μM range are to be expected in the naturally occurring series. Control experiments with Dharmacon-made A-site RNA construct produced the same results as the experiments with A-site construct, synthesized in our laboratory.

Naturally occurring neomycin B binds to the D-A-site RNA construct with an approximately two-fold higher affinity than to the L-RNA construct (Table 2). Overall these results indicate a very modest degree of stereospecificity in aminoglycoside-decoding region rRNA binding.

Figure 7A:
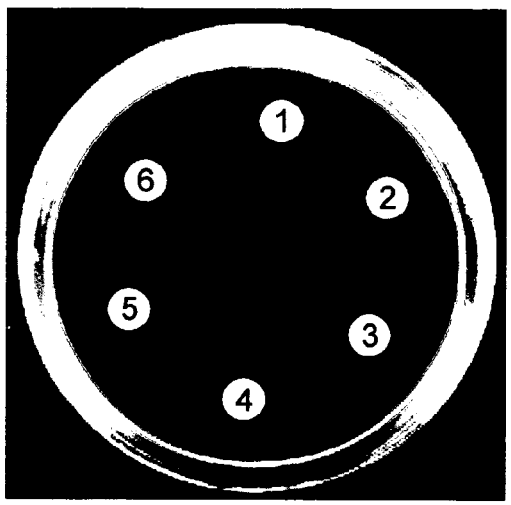
FIG. 7A is a image of an antibiotic activity disk assay of E. coli (ATCC 25922) wild type where each numbered disc is impregnated with an aminoglycoside: 1, D-neamine (100 nmol), 2, D-neamine (200 nmol), 3, D-neamine (500 nmol), 4, L-neamine (200 nmol), 5, L-neamine (500 nmol) 6, L-neamine (1000 nmol)
Figure 7B:
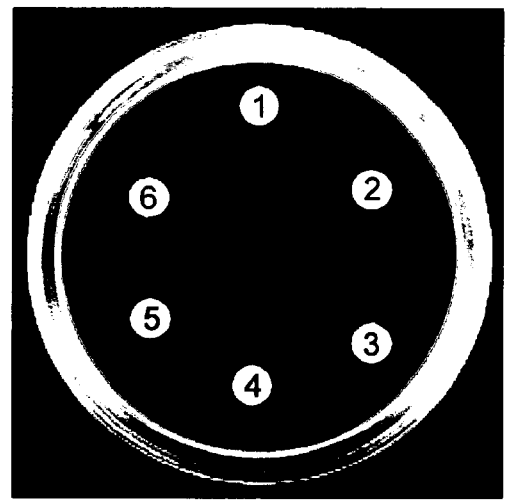
FIG. 7B is a image of an antibiotic activity disk assay of E. coli (ATCC 25922) transformed with the plasmid pMM, bearing the APH(3')IIa gene where each numbered disc is impregnated with an aminoglycoside: 1, D-neamine (100 mmol), 2, D-neamine (200 mmol), 3, D-neamine (500 mmol), 4, L-neamine (200 mmol), 5, L-neamine (500 mmol) 6, L-neamine (1000 mmol)
Figure 7C:
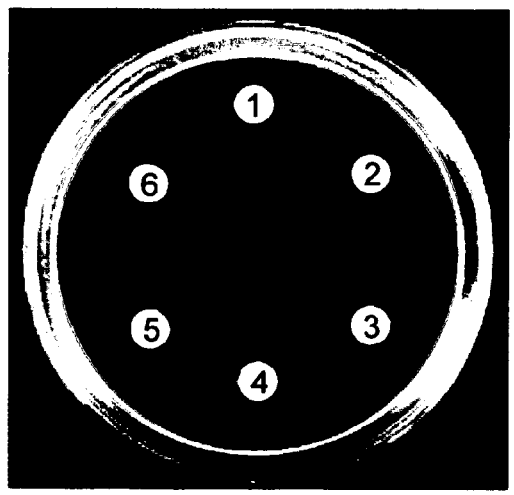
FIG. 7C is an image of an antibiotic activity disk assay of P. aeruginosa (ATCC 27853) where each numbered disc is impregnated with an aminoglycoside: 1, D-neamine (100 nmol), 2, D-neamine (200 nmol), 3, D-neamine (500 nmol), 4, L-neamine (200 mmol), 5, L-neamine (500 mmol) 6, L-neamine (1000 nmol)

The present invention has established that non-stereospecificity in the binding of aminoglycoside compounds to RNA occurs for short RNA constructs as shown in FIG. 9A-C and also for native rRNA, which in certain situations may be complexed with ribosomal proteins. The present invention observed non-stereospecific binding of a D-aminoglycoside and a L-aminoglycoside, e.g., D-neamine and L-neamine, to ribosomes and observed the effect of this binding on bacterial cell growth (FIG. 7A-C).

Binding Sites of D-1L-Neamine and Neomycin B on D- and L-A-Site RNA.

Figure 12:
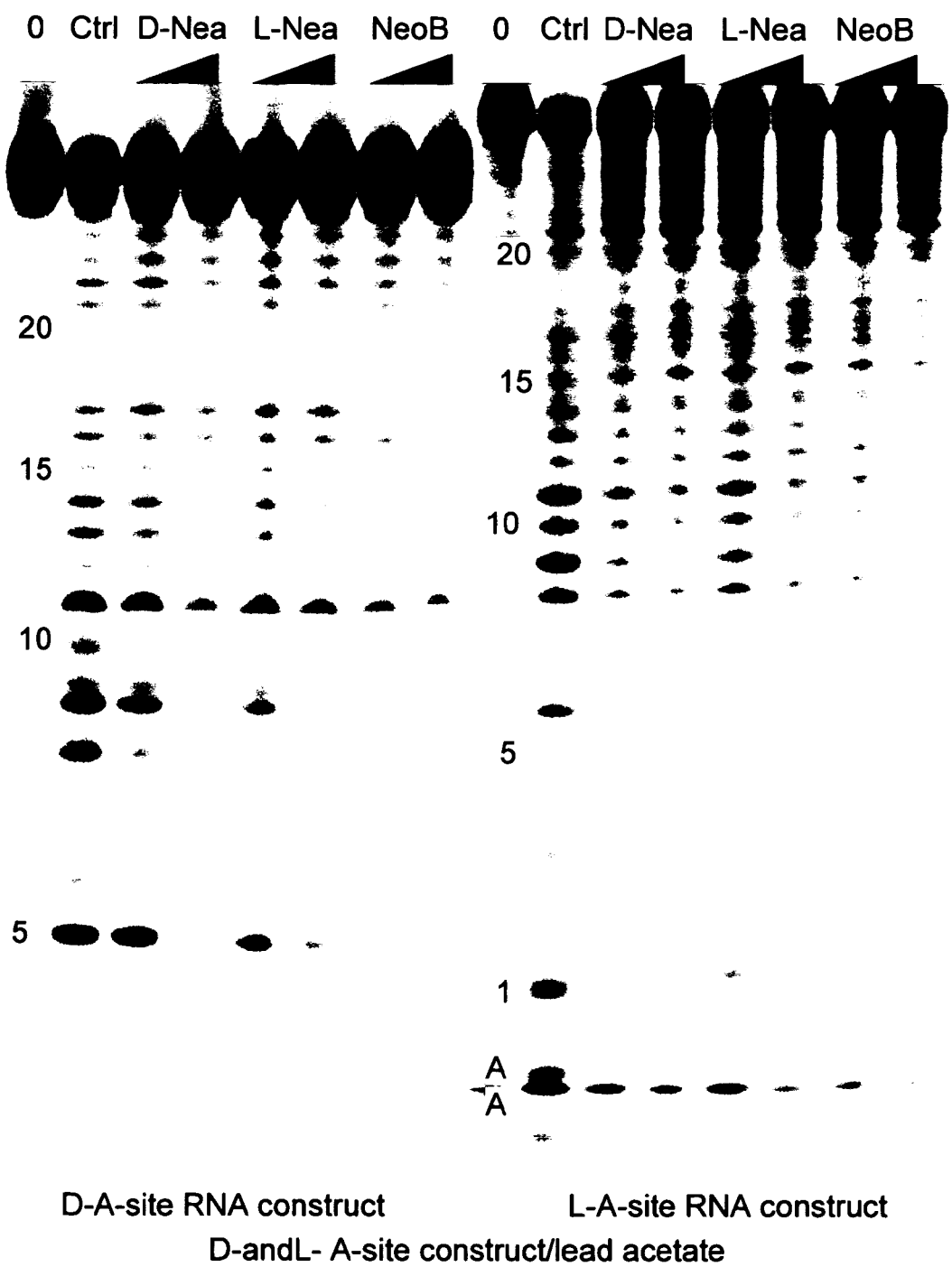
FIG. 12 is an gel-electrophoresis of lead acetate footprinting studies of aminoglycoside binding to D- and L-A-site RNA constructs. 0, untreated A-site RNA ($^{32}$P-labeled at 5' end); Ctrl, control experiment in the absence of binders; D-Nea, L-Nea, NeoB-RNA RNA footprinting in the presence of D-neamine, L-neamine and neomycin B; Concentrations of the aminoglycosides: 25 and 125 μM.

In order to determine whether the enantiomeric aminoglycosides recognize similar features of the A-site RNA binding site, two RNA footprinting techniques (lead acetate and DMS footprinting) were used to reveal the binding sites for the D-, L-neamine and neomycin B on the D- and L-A-site of 16S RNA constructs (FIGS. 12, 13). Both D- and L-RNA (with D-$A_3$ tail) were then $^{32}$P-labeled at the 5' end. In order to achieve enzymatic radiolabeling of L-RNA, the L-A-site construct with a tail of three D-adenosines at 5' end was prepared (FIG. 11). The L-RNA oligonucleotide containing a single D-adenosine at 5' end was radiolabled using T4

TABLE 2

Dissociation Constants, of Aminoglycoside Complexes with D- and L-RNA Constructs (μM). The decoding region constructs were assayed with CRP and D and L-J6f1 were assayed with CRT.

| RNA | CRP/CRT | Neomycin | Paromomycin | Kanamycin | Tobramycin |
|---|---|---|---|---|---|
| D-B | 0.170 ± 0.0175 | 0.05196 ± 0.00186 | 1.65 ± 0.35 | 1.25 ± 0.07 | 1.40 ± 0.24 |
| L-B | 0.224 ± 0.0226 | 0.109 ± 0.0046 | 6.38 ± 0.27 | 0.81 ± 0.095 | 4.39 ± 0.37 |
| D-H | 1.36 ± 0.18 | 0.26 ± 0.0036 | 2.20 ± 0.17 | 1.37 ± 0.21 | 1.57 ± 0.21 |
| L-H | 0.90 ± 0.076 | 1.41 ± 0.014 | 2.76 ± 0.26 | 2.16 ± 0.23 | 3.22 ± 0.26 |
| D-J6f1 | 0.19 ± 0.011 | 5.59 ± 1.39 | ND[a] | 0.022 ± 0.0047 | 0.0052 ± 0.00042 |
| L-J6f1 | 0.20 ± 0.028 | 0.36 ± 0.021 | 4.60 ± 0.37 | 3.34 ± 0.25 | 2.18 ± 0.23 |

[a]not determined

Two issues of importance are worth commenting on. Most importantly, the data shows that aminoglycoside binding to the eukaryotic and prokaryotic decoding region constructs is non-stereospecific. Aminoglycoside binding to the 'control' J6f1 construct on the other hand is stereospecific. Measured binding affinities are consistent with binding measurements on prokaryotic ribosomes using radioactive tobramycin (Le Goffic, F., Capmau, M.-L., Tangy, F., & Baillarge, M. (1979) Eur. J. Biochem. 102, 73-81). Low μM binding affinities are to be expected in the naturally occurring series.

Given the stereochemical results described above, the enantiomeric aminoglycoside L-neamine (Example 1) was synthesized and tested as a competitive inhibitor for CRP binding to the A-site constructs described above (Table 2). The binding of L-neamine to both the D- and L-A-site constructs was compared to the binding of the naturally occurring enantiomer D-neamine. Straightforward competitive binding of L-neamine to the RNA constructs was observed. D-neamine binds with an approximately two-fold higher affinity to the D-construct than does L-neamine (Table 2). Conversely, L-neamine binds with a two-fold higher affinity than D-neamine does to the L-site RNA.

polynucleotide kinase with only 1-3% efficiency, while the three-adenosine tail provided over 25% labeling efficiency.

Figure 14:
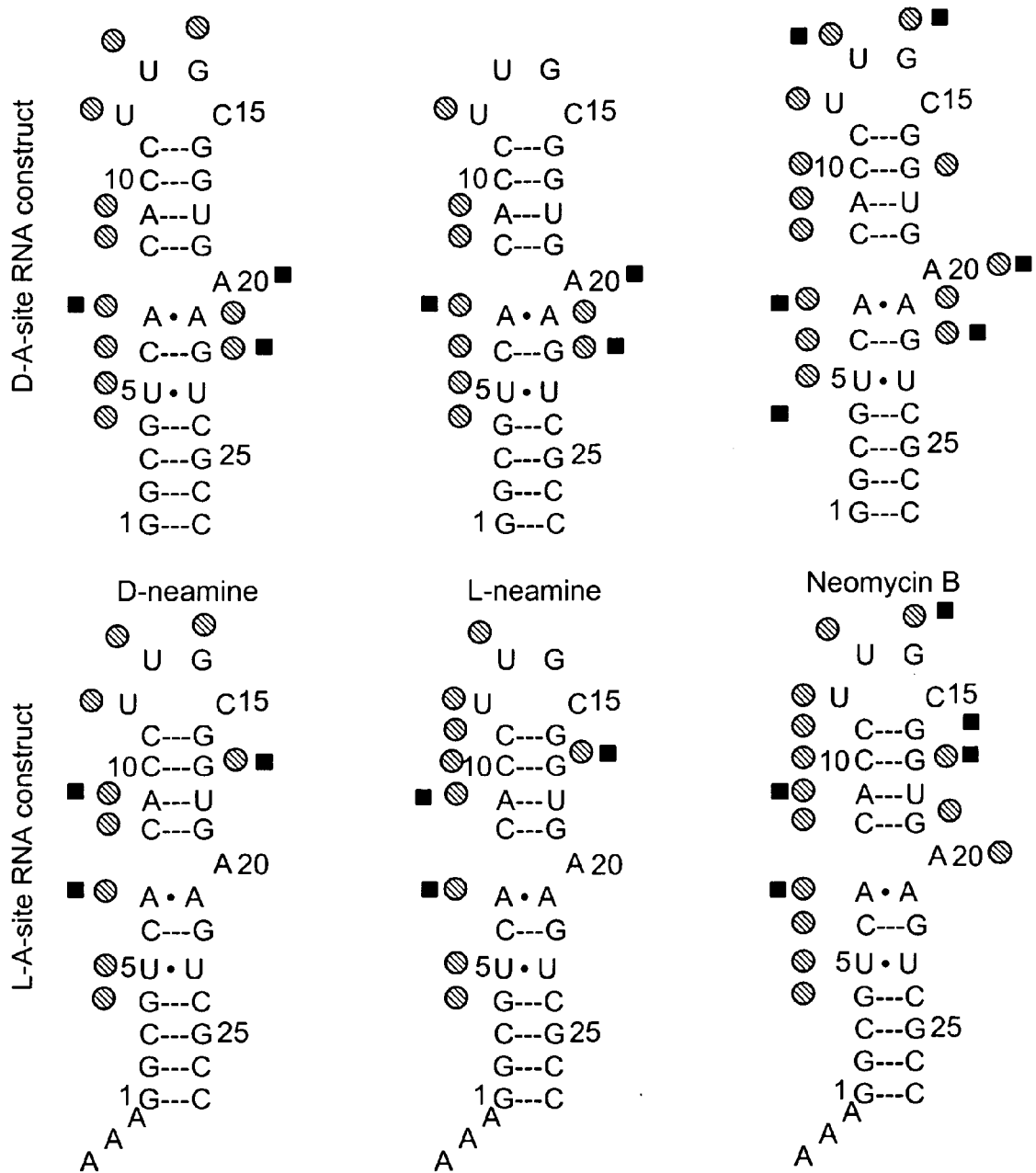
FIG. 14 is a summary of D- and L-A-site RNA construct footprinting studies. Upper row-D-RNA construct, lower row-L-RNA construct. Circles-nucleotides, which found protected by lead acetate footprinting method. Arrows-nucleotides, which found enhanced by lead acetate footprinting method. Squares-nucleotides, which found protected by DMS footprinting method.

A summary of the footprinting results are presented in FIG. 14. Both footprinting methods used in this study indicate that both L- and D-neamine appear to bind to the same site on the D-A-site RNA construct. The binding site is located in the A-rich bulge and part of the stem below it. The putative binding site is formed by nucleotides C6-G22, A7•A21 and A20 (FIG. 14). This site is similar to neomycin B binding site; which is larger and spans C6-G22, and A7•A21, as well as involving G4, U5 and A20. Binding of neomycin B to the D-A-site construct induces a significant conformational change in the RNA structure, protecting tetraloop nucleotides U13 and C14. These results are similar to previously reported specific binding site for aminoglycosides on A-site RNA construct.

The binding of the aminoglycosides to the enantiomeric L-A-site of rRNA constructs was also investigated. Here, both D- and L-neamine again bind similarly, mainly protecting the A-rich bulge region, and the upper stem portion of the L-RNA construct (FIG. 14). Their binding site is formed by A7•A21, A9, C10-G17 nucleotides. Binding of D-/L-neamine to L-A-site construct protects a portion of tetraloop (U12, U13). There is also a clear difference in binding of neomycin B to L-RNA construct as compared to binding to D-RNA construct. The site for neomycin B on L-RNA is formed by A7•A21, C8-G19, A9, C10-G17, C11-G16 and A20, and thus spans the upper-stem and A-rich bulge region. In addition, the tetraloop nucleotide C14 is also involved in the interactions with neomycin B.

Measurement of Aminoglycoside Binding to Ribosomes

In order to establish that observed non-stereospecific binding of aminoglycosides to D-RNA and L-RNA constructs is not limited to the short RNA sequences as depicted in FIG. 9A-C, binding affinities for D-neamine and L-neamine for ribosomes were determined and the effects of neamine on bacterial cell growth measured. Non-stereospecific binding of neamine enantiomers to ribosomes was observed thereby establishing the ability of aminoglycosides to bind native RNA which may optionally be coupled to one or more ribosomal proteins.

The non-stereospecific binding observed for aminoglycosides with the decoding region RNA constructs B and H is a general characteristic of conformationally flexible aminoglycosides with flexible RNA constructs when the binding affinity is one a low micromolar range, e.g., about 0.1 µM to about 100 µM range. The decoding region RNA constructs prepared from either L- or D-ribonucleosides described herein bind aminoglycosides in the µM range, an affinity typical of many aminoglycoside RNA interactions.

The RNA aptamer J6f1, (FIG. 9C) binds tobramycin with a $K_D$=5 nM, and distinguishes in binding among structurally similar aminoglycosides (Table 2), although not as strongly as the full-length constructs. The L-RNA aptamer J6f1, (FIG. 9C) binds tobramycin with a $K_D$=2.2 µM (Table 2), and has thus reverted to the binding affinity typical of many quasi-specific aminoglycoside-RNA binding events, including aminoglycoside binding by the decoding region constructs. Not only has the binding affinity of L-RNA aptamer J6f1, (FIG. 9C) for tobramycin decreased by 420-fold, but the specificity of binding for tobramycin is substantially decreased (Table 2). These experiments demonstrate that stereospecificity of aminoglycoside binding does occur in the case of specific tight binding RNA aptamers, and is not simply a function of innate ligand-receptor flexibility. Although not wanting to be bound by theory, aminoglycosides with binding affinities having a $K_D$ in the nanomolar range appear to have one or more stereospecific interactions with target RNA sequences and aminoglycosides which bind RNA sequences with a $K_D$ in the micromolar range, e.g., 0.1 µM to about 100 µM, exhibit non-stereospecific binding interactions.

After establishing the lack of stereospecificity in the binding of aminoglycosides to the A-site RNA constructs (FIG. 9A-C) where the binding affinity, $K_D$, is about 0.1 µM to about 100 µM, the stereospecificity of aminoglycoside binding to intact ribosomes was determined. Both yeast and E. coli ribosomes were prepared and aminoglycoside binding was measured using fluorescence anisotropy methods. For example, fluorescence anisotropy methods recited in Wang, Y., and Rando, R. R. Chem. Biol. (1995) 2, 281-290; and Wang, Y., Hamasaki, K., and Rando, R. R. Biochemistry (1997) 36,768-779. CRP was used as the binding probe. The fluorescence assay was found to be well adapted to measuring aminoglycoside binding to 70S bacterial (E. coli) and 80S ribosomes (yeast). Save for neomycin B where the dissociation constant is approximately 0.1 µM, the typical dissociation constants for aminoglycoside-RNA aptamer complexes are in the 1-2 µM range. These data are quite consistent with measurements made on the A-site decoding region constructs and data from direct measurements on radioactive aminoglycoside binding to intact E. coli ribosomes. In addition, streptomycin, which is not thought to bind with high affinity to the A-site decoding region in bacteria, did not exhibit measurable binding in the 70S ribosomes (E. coli). Binding data reported herein for aminoglycoside compounds with eukaryotic yeast ribosomes are similar to binding data for said aminoglycoside compounds with ribosoimes in bacteria and with eukaryotic A-site rRNA constructs.

Figure 4A:
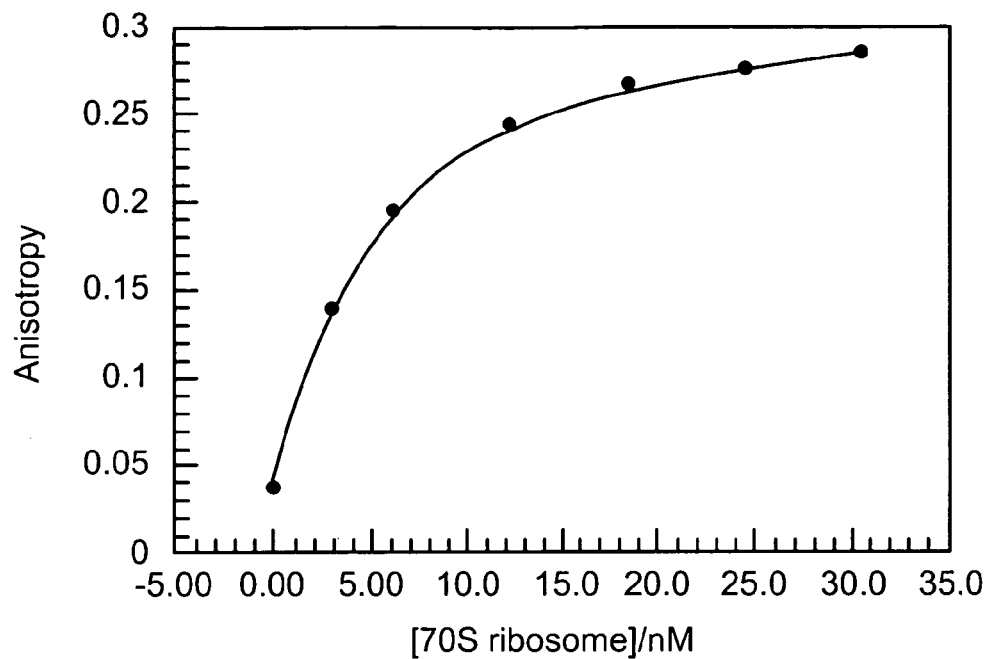
FIG. 4A is a plot of fluorescence anisotropy of fluorescently labeled paromomycin (CRP) (20 nM) as a function of 70S ribosome concentration.
Figure 4B:
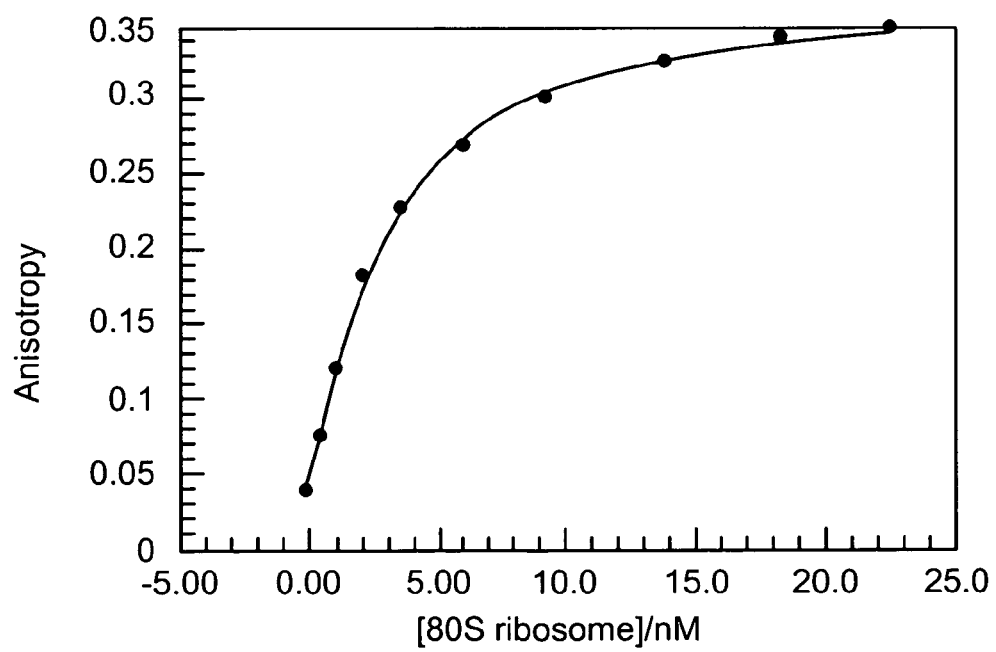
FIG. 4B is a plot of fluorescence anisotropy of fluorescently labeled paromomycin (CRP) (20 nM) as a function of 80S ribosome concentration.
Figure 5A:
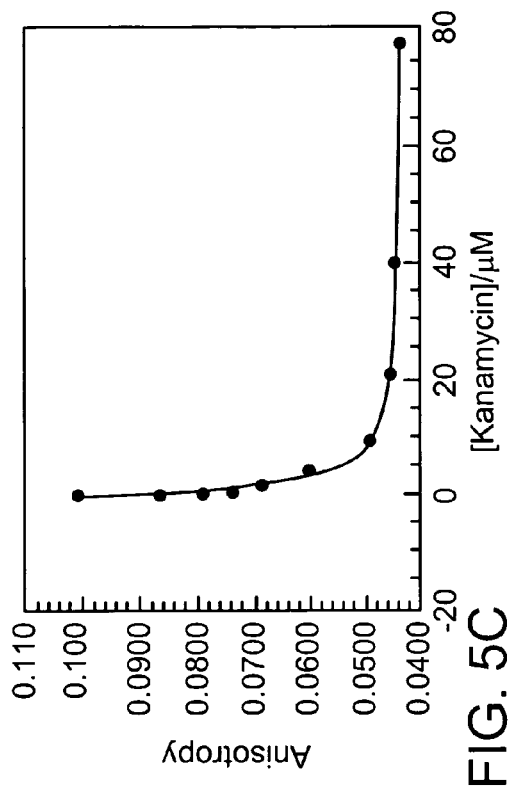
FIG. 5A is a plot of fluorescence anisotropy of fluorescently labeled paromomycin (CRP) (20 mM) containing 70S ribosomes, as a function of neomycin concentration.
Figure 5B:
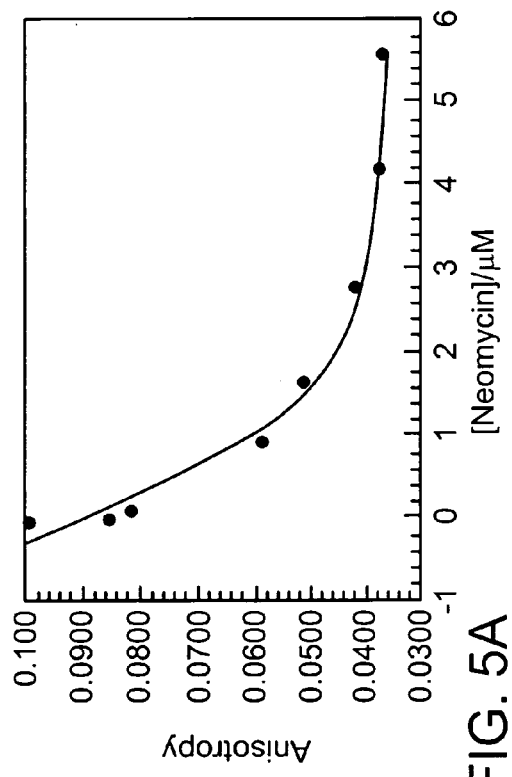
FIG. 5B is a plot of fluorescence anisotropy of fluorescently labeled paromomycin (CRP) (20 nM) containing 70S ribosomes, as a function of paromomycin concentration.
Figure 5C:
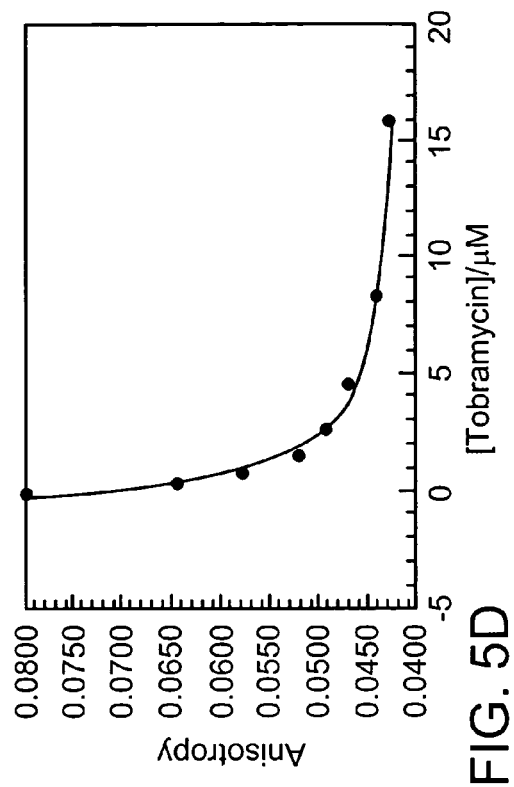
FIG. 5C is a plot of fluorescence anisotropy of fluorescently labeled paromomycin (CRP) (20 nM) containing 70S ribosomes, as a function of kanamycin concentration.
Figure 5D:
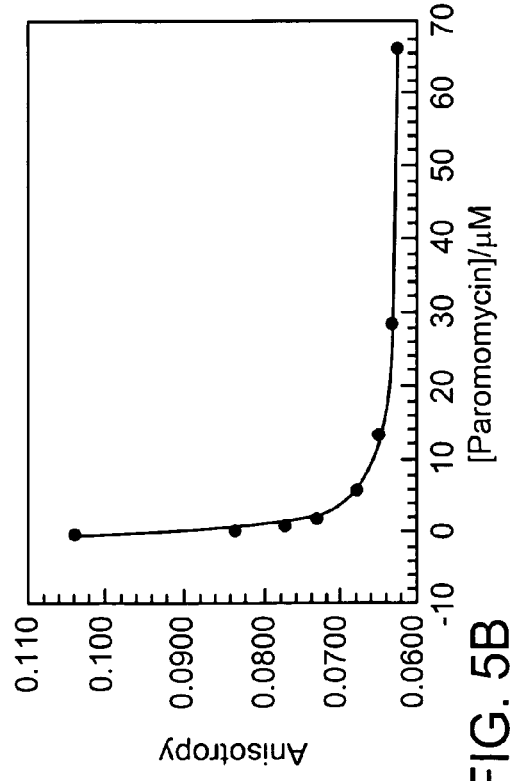
FIG. 5D is a plot of fluorescence anisotropy of fluorescently labeled paromomycin (CRP) (20 nM) containing 70S ribosomes, as a function of tobramycin concentration.

In initial experiments, it could be readily shown that CRP saturably bound with high affinity to both E. coli (70S) and yeast (80S) ribosomes (FIG. 4A, B). Moreover, competition with several aminoglycosides provided binding data quite consistent with expectations. Competition binding data for complexation of neomycin, paromomycin, kanamycin, and tobramycin to 70 S ribosomes is presented in FIG. 5A-D. Streptomycin does not effectively compete with CRP binding to bacterial ribosome, an expected result given that streptomycin does not effectively bind to the aminoglycoside binding domain of ribosomes under standard conditions. The binding data are summarized in Table 3. These data are in reasonable accord with published measurements made using a radio ligand binding assay. For example, tobramycin and kanamycin were reported to bind with $K_D$=1.4 µM and 1.7 µM respectively.

Similar experiments were performed with yeast 80S ribosomes. It was established that aminoglycoside antibiotics bind to E. coli and yeast ribosomes with comparable affinities (Table 3). Interestingly, streptomycin was found to compete with CRP for 80S ribosome binding, producing $K_D$ value of 30.5 µM, which indicates a certain difference between the mode of streptomycin interaction with 80S and 70S ribosomes.

TABLE 3

Dissociation constants for complexes of aminoglycosides with 70S and 80S ribosomes (µM).

| Aminoglycoside | 70S Ribosome | 80S Ribosome |
| --- | --- | --- |
| CRP ($K_d$) | 0.0037 ± 0.0011 | 0.0032 ± 0.0009 |
| Neomycin | 0.14 ± 0.038 | 0.11 ± 0.014 |
| Paromomycin | 1.41 ± 0.15 | 1.97 ± 0.10 |
| Kanamycin | 1.51 ± 0.46 | 2.63 ± 0.52 |
| Tobramycin | 1.76 ± 0.38 | 3.69 ± 0.31 |
| Streptomycin | NB | 30.5 ± 2.33 |
| D-Neamine | 5.45 ± 0.68 | 1.14 ± 0.25 |
| L-Neamine | 2.69 ± 0.46 | 6.06 ± 0.63 |

Binding affinities of D, L-neamine 1, ent-1 and their isomers 2, 3, ent-2, ent-3 (Table 1) to ribosomes were determined by the competitive binding assay using the fluorescence anisotropy method recently developed in our laboratory. The binding results are summarized in Table 4. All of D, L-neamine and their isomers bind to ribosomes with dissociation constats in the 0.9~33 µM range. 5-Isomers of neamines, 2 and ent-2 shows better binding affinities to bacterial ribosome than other positional isomers. 4-Isomer of L-neamine ent-3 shows the highest preference for the bacterial ribosome, fivefold over eukaryotic, yeast ribosome. Both D- and L-neamine bind to E. coli and yeast ribosomes with comparable affinities. Because bacterial resistance to aminoglycosides most frequently occurs through enzymatic acetylation, phosphorylation and ribosylation with specificity, this kinds of enantiomeric and positional neamines can be used as useful scaffolds for developing unnatural aminoglycosides which escape these resistance mechanisms but still be effective in binding to their bacterial target ribosome.

TABLE 4

Dissociation Constants of D-, L-Neamine and their isomers for Ribosomes. ($K_D$, μM)

| Aminoglycosides | 70S ribosome(*E. coli.*) | 80S ribosome(yeast) |
|---|---|---|
| D-Neamine (1) | 5.45 ± 0.68 | 1.14 ± 0.25 |
| 5-Isomer of D-Neamine (2) | 0.91 ± 0.13 | 2.22 ± 0.11 |
| 6-Isomer of D-Neamine (3) | 30.73 ± 1.7 | 22.47 ± 1.25 |
| L-Neamine (ent-1) | 2.69 ± 0.46 | 6.06 ± 0.63 |
| 5-Isomer of L-Neamine (ent-2) | 1.55 ± 0.11 | 1.53 ± 0.12 |
| 4-Isomer of L-Neamine (ent-3) | 6.40 ± 0.87 | 33.0 ± 5.84 |

Binding of D and L-Neamine to Bacterial and Yeast Ribosomes

Figure 6A:
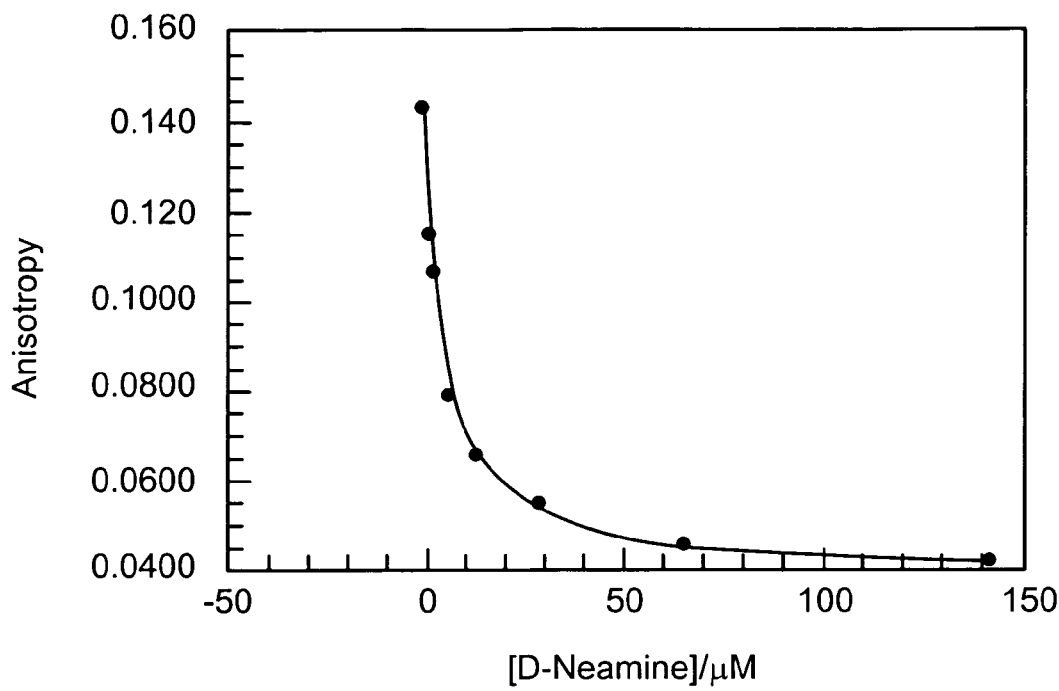
FIG. 6A is a plot of fluorescence anisotropy of fluorescently labeled paromomycin (CRP) (20 nM) containing 70S ribosome as a function of D-neamine concentration.
Figure 6B:
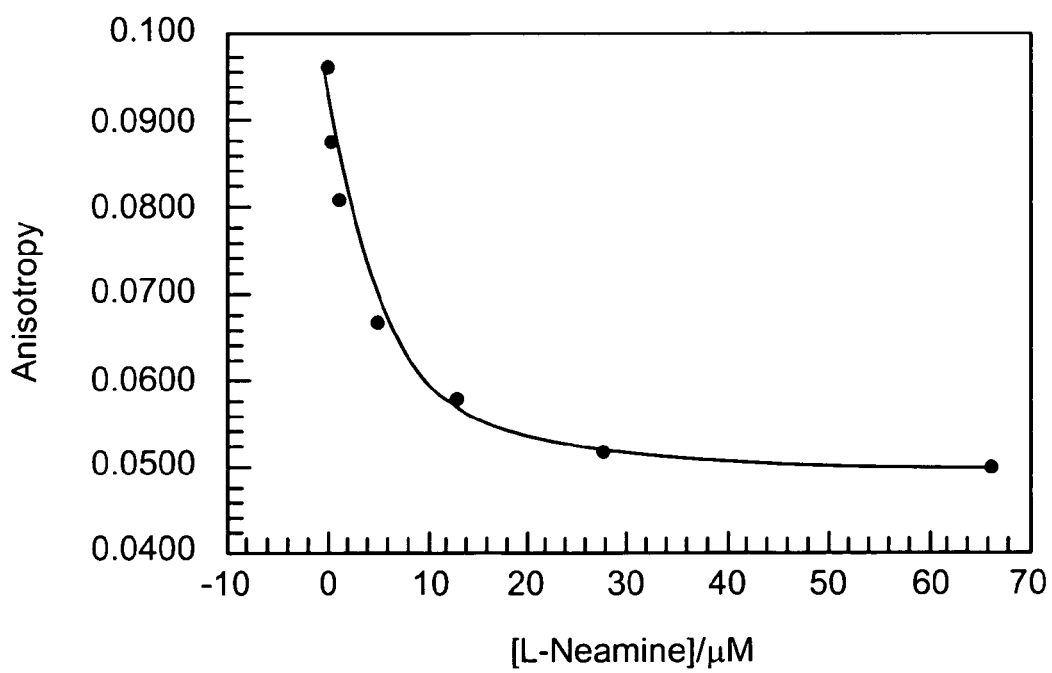
FIG. 6B is a plot of fluorescence anisotropy of fluorescently labeled paromomycin (CRP) (20 nM) containing 70S ribosome as a function of L-neamine concentration.

The stereospecificity of aminoglycoside binding to *E. coli* and yeast ribosomes was then determined using the fluorescence method described above using D and L-neamine as the competing aminoglycosides. The competitive binding isotherms for the binding of D and L-neamine are shown in FIGS. 6A, B and the binding data for the isomers are summarized in Table 4. Most importantly, both L and D-neamine bind to *E. coli* and yeast ribosomes with comparable affinities. In fact, L-neamine bound to *E. coli* ribosomes with a two-fold greater affinity than did D-neamine. Small and large subunits were not tested independently because while the A-site decoding region resides on the small 30S subunit, there is also some measured aminoglycoside binding associated with the larger 50S subunit. These experiments demonstrate that the binding of aminoglycosides to ribosomes is non-stereospecific as well. In order to determine if the binding of L-neamine had functional consequences to the growth of WT *E. coli* (ATCC 25922), the growth inhibitory effects of this aminoglycoside was compared to that of D-neamine. Importantly, both D and L-neamine were growth inhibitory, and therefore the binding of L-neamine to ribosomes has the same functional consequence as the binding of D-neamine. It should be noted though that the natural D-neamine proved to be eight to nine-fold more potent than its enantiomer. The reason for the lower in vivo activity of the L-enantiomer is not clear, but it may be related to cellular uptake. While the actual mechanism of membrane permeability to cationic aminoglycosides has not been clarified on a molecular level, it is likely that the process involves membrane channels. It is then possible that the transmembrane transport of aminoglycosides behaves stereoselectively, and that L-neamine is transported with lowered efficiency compared to its enantiomer. L-neamine, like other aminoglycosides, is bactericidal and exhibits very weak activity against Gram-(+) bacteria-another hallmark of aminoglycosides. For example, when L-neamine was tested against *S. aureus* and *E. faecalis* little to no antibacterial activity was found. Antibacterial activity of the neamine enantiomers against aminoglycoside resistant bacteria was also determined.

The finding that our flourescence binding assay can be used for determining binding affinities to ribosomes allowed us to determine whether aminoglycoside binding to ribosomes is stereospecific or not. These experiments were carried out with naturally occurring, D-neamine and its synthetic enantiomer L-neamine. The competitive binding isotherms for the binding of D and L-neamine are shown in FIGS. 6A, B and the binding data for the isomers are compiled in Tables. 3 and 4. Most importantly, both L and D-neamine bind to *E. coli* and yeast ribosomes with comparable affinities. L-neamine actually binds to the bacterial ribosome with an approximately two-fold higher affinity than the natural D-neamine. In the case of the yeast ribosome, D-neamine binds with a greater affinity. These experiments establish that aminoglycoside binding to the intact ribosome is non-stereospecific, and therefore, that the results obtained with the A-site rRNA constructs are predictive of ribosomal binding for L-aminoglycoside compounds.

Inhibition of Translation by D- and L-Neamine.

Figure 10A:
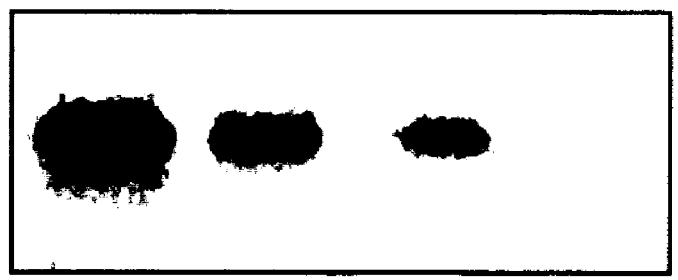
FIG. 10A is a gel-electrophoresis for In vitro protein translation in the presence of neomycin B.
Figure 10B:
FIG. 10B is a gel-electrophoresis for In vitro protein translation in the presence of D-neamine.
Figure 10C:
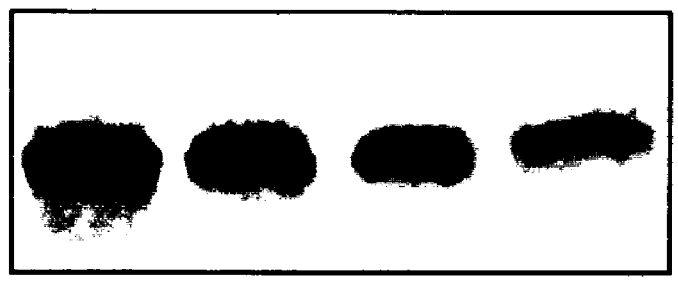
FIG. 10C is a gel-electrophoresis for In vitro protein translation in the presence of L-neamine.

In order to determine the functional consequences of D/L-neamine binding to ribosomes, the effects of these aminoglycosides on protein translation were determined. D- and L-neamine were analyzed with regard to their potencies as inhibitors of in vitro translation. Neomycin B was used as a control aminoglycoside. FIG. 10 shows the results of typical in vitro translation reactions in the presence of neomycin B (A), D-neamine (B) and L-neamine (C). As expected, the aminoglycosides were found to effectively inhibit in vitro translation. $IC_{50}$, 50% inhibitory concentration, was defined as concentrations of aminoglycoside producing 50% inhibition of translation. Quantitation of the gel bands provided the following $IC_{50}$ values: neomycin B—15 μM; D-neamine—38 μM and L-neamine—195 μM. These functional assays indicate a clear stereoselective advantage of D-neamine versus its unnatural L-neamine enantiomer.

Protein translation was performed from chloramphenicol acetyl transferase (CAT) mRNA. CAT mRNA was transcribed from a plasmid, bearing the CAT gene under the control of T7 promotor (PROTEINscript™-PRO Linked Transcription:Translation kit. *Ambion® instruction manual*; and Pratt J. M. (1984) Coupled transcription-taanslation in prokariotic cell-free system. In *Transcription and Translation* (Hames, B. C., and Higgins, S. J.), pp 179-209, RL Press, Oxford). A commercial *E. coli* ribosomal suspension was supplemented with an *E. coli* extract containing the required elements for translation. These include translation factors, tRNAs, and aminoacyl tRNA synthases. Plasmid, T7 RNA polymerase and amino acids were added to the reaction mixture, and both transcription and translation steps were performed in the same vial. The effects of the aminoglycosides on the translation process were evaluated by measuring the incorporation of $^{35}S$ methionine in the translated chloramphenicol acetyl transferase protein. Both D- and L-neamine are capable of the inhibiting protein synthesis in vitro. However, D-neamine appeared over 5-fold more potent as a translation inhibitor than L-neamine. This result shows that the ribosomal binding data per se is not quantitatively predictive with respect to the functional potencies of aminoglycosides. The 70S ribosomal binding studies actually showed a small two-fold difference in binding affinity between D- and L-neamines, with the L-neamine binding with greater affinity. In the functional assay D-neamine proved to be approximately 5-fold more potent than its enantiomer. There are at least two possible reasons for this observed disparity. First, it is possible that the measurements of ribosome-aminoglycoside binding provide average dissociation constants for several different binding sites with similar dissociation constants. Only binding at the A-site is crucial for the inhibition of translation. The notion of multiple aminoglycoside binding sites runs counter to previous chemical protection experiments performed on ribosomes, not to mention NMR and X-ray structural studies, which suggest a localized binding-site for aminoglycosides at the decoding region (Fourmy, D., Recht, M. I., Blanchard, S. C. and Puglisi, J. D. (1996) *Science* 274, 1367-1371; Lynch, S. R. and Puglisi, J. D. (2001) *J. Mol. Biol.* 306, 1037-1058; Wimberly, B. T., Brodersen, D. E., Clemons, W. M., Jr., Morgan-Warren, R. J., Carter, A. P., Vonrhein, C., Hartsch, T. and Ramakrishnan, V. (2000) *Nature* 407, 327-339; and Carter, A. P., Clemons, W. M., Brodersen, D. E., Morgan-Warren, R. J., Wimberly, B. T. and Ramakrishnan, V. (2000) *Nature* 407, 340-348). However, binding measurements and chemical protection experiments measure entirely different phenomena. In fact, given the broad range of RNA structures that aminoglycosides bind to it would be surprising if a structure as complicated as a ribosome only possessed a single aminoglycoside binding-site. A second reason for the disparity in measurements is that it is entirely possible that the structure of the decoding region is altered during translation. This could have the effect of altering binding affinities for aminoglycosides, so that binding measurements made on quiescent ribosomes are not quantitatively relevant to aminoglycoside binding to ribosomes during translation, with all of the various factors and mRNA interacting with the ribosome.

Antibiotic Activity Disk Assay

In preferred embodiments of the present invention, L-aminoglycosides such as L-neamine maintains antibiotic activity against bacterial strains resistant to D-aminoglycosides. For example, when a wild type *E. coli* strain was transformed with plasmid pMM bearing the gene for the aminoglycoside kinase APH(3')IIa, which confers kanamycin resistance, the transformed strain had selective resistance towards D-neamine, but L-neamine maintained antibiotic activity. Moreover, when D- and L-enantiomers of neamine were tested against a naturally aminoglycoside resistant *P. aerugenosa* strain, the observed antibiotic activities of the D- and L-neamine enantiomers proved to be substantially the same, suggesting enhanced resistance of this strain to D-neamine because D-neamine is about 9 times more active against non-resistant strains.

Aminoglycoside metabolizing enzymes, including APH (3')Iia, acetylases, the adenylylases, and the linases, are stereospecific for D-aminoglycoside substrates. L-aminoglycosides enantiomers any avoid common cellular resistance mechanisms which degrade or otherwise deactivate their corresponding D-enantiomer, including enzymatic degredation which targets D-aminoglycoside substrates, while maintaining effective binding to their target bacterial rRNA molecules. Since bacterial resistance to the aminoglycosides most frequently occurs through extrinsic, metabolic means, and not through mutations in the target rRNAs, aminoglycoside analogs which escape these modification reactions could be of substantial use as antibiotics and other applications where resistance to enzymatic degradation would be advantageous.

The anti-bacterial effects of L-aminoglycoside compounds of the invention were determined suing two Gram-(−) strains were investigated, *E. coli* (ATCC 25922) and *P. aerugenosa* (ATCC 27853). These two strains were chosen because: (1) both strains are Gram-(−) and aminoglycosides preferentially inhibit the growth of Gram-(−) bacteria; and (2) both strains are potentially resistant to aminoglycosides by mechanisms involving the enzymatic modification of these drugs. An attractive property of L-aminoglycoside compounds of the invention is that they might avoid resistance mechanisms that depend on stereospecific interactions between modifying enzymes and their aminoglycoside substrates.

L-aminoglycosides such as L-neamine possess antibacterial activity. The antibacterial activitity of L-neamine and D-neamine were studied using antibiotic disk assays. L-neamine displayed a somewhat lower activity with WT *E. coli* (ATCC 25922) than D-neamine (FIG. 7A), but L-neamine is still clearly active. Interestingly, when a disk assay using an *E. coli* bacterial stain that is resistant to kanamycin/ neomycin were studied, the activity of D-neamine was essentially abolished, while L-neamine maintaines substantially the same level of activity as observed for disc assays with WT *E. coli* (FIG. 7B).

Aminoglycoside resistance of *E. coli* was induced by transformation with pMM plasmid. This plasmid contains the neomycin phosphotransferase gene, NTP II, derived from the Tn5 transposon, a generic antibiotic marker for kanamycin/neomycin resistance. The protein product of the NTP II gene is the APH(3')IIa phosphotransferase. This gene is derived from the Tn5 transposon, and comprises a generic antibiotic marker for kanamycin and neomycin resistance (Wright, G. D. and Thompson, P. R. (1999) *Front. Biosci.* 4, D9-21). In a second set of experiments, the sensitivity of *P. aerugenosa* (ATCC 27853) towards the L- and D-neamine enantiomers was studied. Both D-neamine and L-neamine showed similar antibiotic activities (FIG. 7C). *P. aeruginosa* contains gene for APH(3')IIb phosphotransferase, homologous to APH(3')IIa which provides the inherent kanamycin resistance of *P. aeruginosa*. It is possible that the enhanced antibiotic activity relative (with respect to WT *E. coli*) activity of L-neamine observed here is related to the selective deactivation of D-neamine. See, for example, Wright, G. D. & Thompson, P. R. (1999) Front. Biosci. 4, D9-21.

Minimal Inhibitory Concentrations of the D- and L-Neamine Enantiomers.

Figure 8:
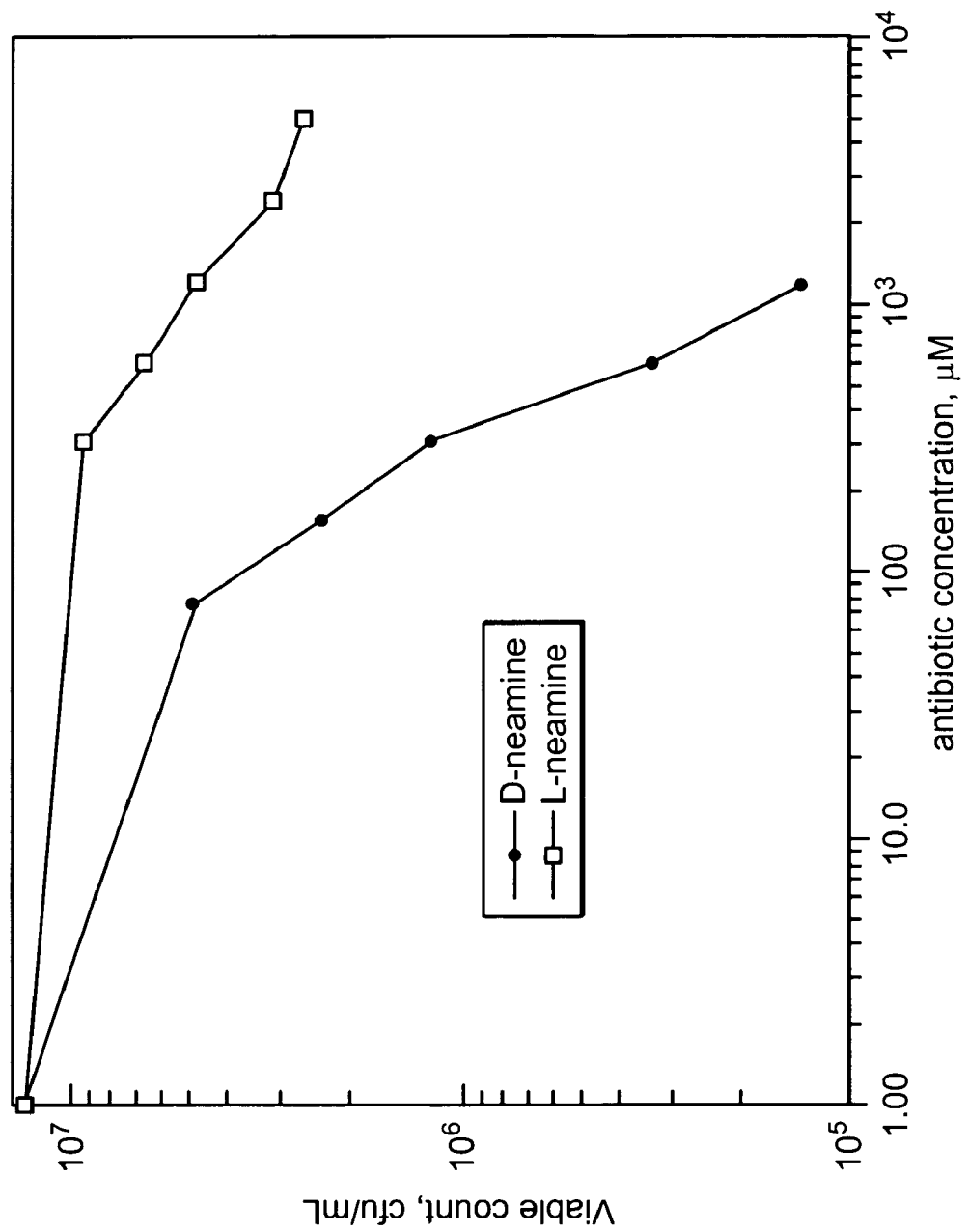
FIG. 8 is a plot of bactericidal profiles of D- and L-neamine against E. coli (ATCC 25922) after a 3 h incubation with antibiotics. Each point is the average of duplicate measurements.

Minimal inhibitory concentrations (MIC) of D- and L-neamine were measured in WT bacterial strains, in kanamycin/neomycin resistant *E. coli*, and in *P. aeruginosa*. The results are summarized in Table 5. The bactericidal profiles for D- and L-neamine are presented in FIG. 8. As can be seen here, both compounds are bactericidal towards *E. coli* (ATCC 25922). However the activity of L-neamine is significantly lower then the activity of natural D-neamine under the conditions of the experiments. D-neamine begins to kill bacteria at 75 µM, while the bactericidal effects of L-neamine are manifest 600 µM and, thus, L-neamine is approximately 8 times less potent than its D-enantiomer. This ratio is confirmed by MIC measurements as L-neamine is observed to be approximately 8.7 times less active than D-neamine. Although the MIC values for L-neamine are close for the resistant and susceptible bacterial strains, there is a sharp drop off for D-neamine in the resistant strains. This is especially true for the resistant *E. coli* strain (Table 5)

TABLE 5

Minimal inhibitory concentrations (MIC) of D- and L-neamine (µM) against wild type and kanamycin/neomycin resistant *E. coli* and *P. aeruginosa*.

| Compound | *E. coli* | *E. coli* kan/neo resistant | *P. aeruginosa* |
|---|---|---|---|
| D-Neamine | 150 | >6400 | 500 |
| L-Neamine | 1300 | 2100 | 1600 |

The following non-limiting examples are illustrative of the invention. All documents mentioned herein are incorporated herein by reference in their entirety.

Experimental Procedures

Neomycin sulfate, paromomycin sulfate, kanamycin B sulfate. tobramycin sulfate, streptomycin sulfate were purchased from Sigma Inc. and used without further purification. 5-Carboxytetramethylrhodamine-labeled paromomycin (CRP) and tobramycin (CRT) were prepared as previously reported (19). L-ribonucleoside phosphoramidites and L-ribonucleoside CPG supports were from Chemgenes Inc. Nick Sephadex G-50 columns were purchased from Pharmacia Inc. D-Neamine hydrochloride was synthesized from Neomycin sulfate as described previously (20).

EXAMPLE 1

The synthesis of L-Neamine Hydrochloride

The synthesis of pseudodissaccharide 1-3 and ent-1-ent-3 was accomplished by glycosylation reaction of properly protected 2-deoxystreptamine acceptors 4, 6 and D, L-glucosamine derivative donors 13, ent-13 (Scheme 1). To secure the required 5,6-positional isomers, relatively small methoxymethyl (MOM) group was considered as 4-hydroxyl protection group of 2-deoxystreptamine (Table 1). The synthesis of glycosyl acceptor 6, donors 13 and its enantiomer, ent-13 is illustrated in Scheme 1. MOM protected 2-deoxystreptamine acceptor 6 was prepared from known diacetylated 2-deoxystreptamine derivative 4(Greenberg, W. A., Priestley, E. S., Sears, S. P., Alper, P. B., Rosenbohrn, C., Hendrix, M., Hung, S.-C., & Wong, C.-H. (1999) J. Am. Chem. Soc. 121, 6527-6541). MOM protection and acetate removal provided acceptor 2 in 96% yield. D-thioglycoside donor 13 was synthesized from protected Dglucosamine derivative 8 (Aiper, P. B., Hung, S.-C. Wong, C.-H. tetrahedron lett. 1996, 34, 6029-6032) in five steps. Compound 8 was converted to the phenylthioglycoside 9 (α/(β=1/1.6) in 90% yield by treatment with phenylthiotrimethylsilane and zinc iodide in dichloroethane (Buskas, T., Garegg, P. J., Konradsson, P., Maloisel, J.-L. Tetrahedron Asymm. 1994, 5, 2187-2194). Acetate deprotection of 9 affoded triol 10, which was monotosylated to give 11 in 94% yield. The tosylate 11 was displaced with sodium azide in DMF providing 12 in quantitative yield. Dibenzylation of 12 gave D-thioglycoside donor 13 (α/β=1/1) in 86% yield. On the other hand the enantiomer of 13, ent-13 (α/β=1/1) was obtained from L-glucosamine derivative 8 (Lin, C.-H., Sugai, T., Haicomb, R. L., Ichikawa, Y., Wong, C.-H. J. Am. Chem. Soc. 1992, 114, 10138-10145) by the same sequence as described.

Scheme 1.
Synthesis of Glycosyl Acceptors 5a, Donors 8b and ent-8b[a]

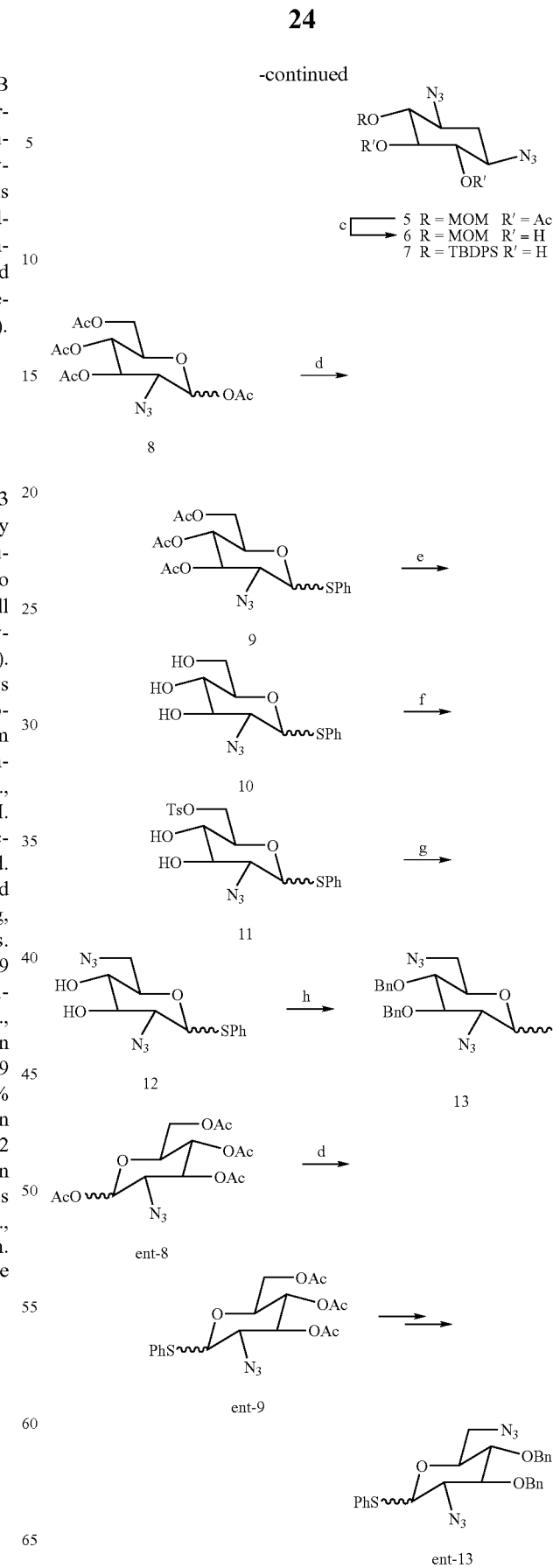

-continued

<sup>a</sup>Reagents and conditions:
a) CH<sub>2</sub>(OCH<sub>3</sub>)<sub>2</sub>, CHCl<sub>3</sub>, P<sub>2</sub>O<sub>5</sub>, 96%
c) NaOMe, MeOH, 100%
b)(i) tBuSi(Ph)<sub>2</sub>Cl, ClCH<sub>2</sub>CH<sub>2</sub>Cl, imidazole, 70° C.
  (ii) NaOMe, MeOH, 80%
c) NaOMe, MeOH, 100%
d) PhSSi(CH<sub>3</sub>)<sub>3</sub>, ZnI<sub>2</sub>, ClCH<sub>2</sub>CH<sub>2</sub>Cl, 50° C., 90%
e) NaOME, MeOH, 98%
f) toluenesulfonyl chloride, pyridine, 94%
g) NAN<sub>3</sub>, DMF, 80° C., 100%
h) BnBR, NaH, DMF, 86%

For the synthesis of D-neamine and 4-positional isomer of L-neamine, 2-deoxystreptamine acceptor 4 was glycosylated with D-thioglycoside donor 13 or its enantiomer ent-13, providing pseudodissaccharide 14, and ent-15, respectively, after deacetylation, in 74% and 73% yield (Scheme 2). While the α/β selectivity of the glycosylation reaction with D-donor 13 was 10:1, the reaction with ent-13 under the same conditions furnished ent-9 in better selectivity (α/β=50/1). In order to get 5,6-positional isomers, glycosylation reactions were performed with MOM protected acceptor 6 and donor 13 or ent-13. After deprotection of MOM and chromatographic separation, 5-hydroxy glycosylated pseudodissaccharide 15 and 6-hydroxy glycosylated isomer 16 were obtained in 30 and 37% yield, respectively, along with mixture of the corresponding b isomers in 15% yield. On the other hand, subsequent glycosylation with L-donor, ent-13 and MOM deprotection provided 14% of 5-isomer ent-15, 46% of 6-isomer ent-14 and also 15% of β isomers mixture.

Scheme 2
Synthesis of D-Neamine (1), L-Neamine (ent-1)
and its positional isomers (2, 3, ent-2 and ent-3).<sup>a</sup>

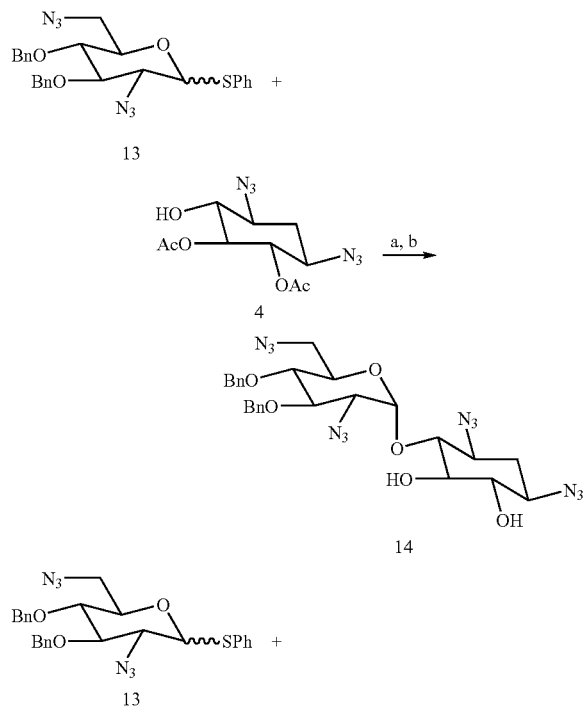

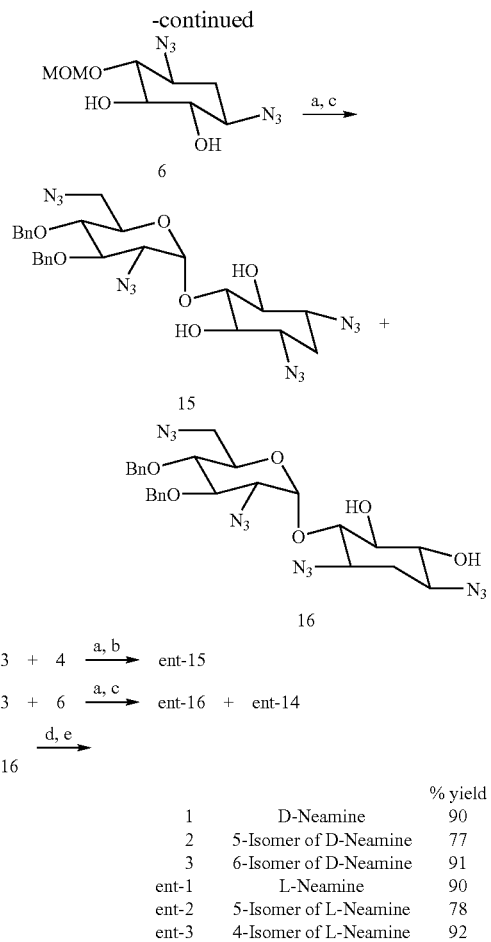

|   |   | % yield |
|---|---|---|
| 1 | D-Neamine | 90 |
| 2 | 5-Isomer of D-Neamine | 77 |
| 3 | 6-Isomer of D-Neamine | 91 |
| ent-1 | L-Neamine | 90 |
| ent-2 | 5-Isomer of L-Neamine | 78 |
| ent-3 | 4-Isomer of L-Neamine | 92 |

<sup>a</sup>Reagents and conditions:
a) N-iodosuccinimide,
   silver trifluoromethanesulfonate,
   Et<sub>2</sub>O/CH<sub>2</sub>Cl<sub>2</sub> = (3/1), −15° C.,
b) NaOMe, MeOH
c) 1N HCl, MeOH, 75° C.
d) P(CH<sub>3</sub>)<sub>3</sub>, THF/0.1N NaOH
e) H<sub>2</sub>, 20% Pd(OH)<sub>2</sub>/C, AcOH/H<sub>2</sub>O Finally, the resulting azides of 14-16(12) and ent-14-ent-16 were subjected to Saudinger reaction condition, followed by catalytic hydrogenation, to furnish D-neamine 1, its 5-isomer 2,6-isomer 3, L-neamine ent-1, its 5-isomer ent-2 and 4-isomer ent-3(13), in 77-92% yield (Scheme 2).

EXAMPLE 2

Synthesis of L and D-Oligonucleotides

The oligomers were synthesized on an Applied Biosystems INC (ABI) 381A DNA/RNA synthesizer using a modified 1 µmol RNA cycle, L(D)-ribonucleoside CPG supports, L(D)-ribonucleoside phosphoramidites and a coupling time of 600 seconds. After deblocking with ethanolic ammonium hydroxide and triethylamine trihydrofluoride, the oligoribonucleotides were precipitated from n-butanol at −20° C. (21) and purified by Nick Sephadex G-50 column. Circular dichroism (CD) spectra were recorded in 0.1M NaCl and 10 mM sodium phosphate, pH 7.0 at 4° C. on an Aviv 202 spectropolarimeter.

EXAMPLE 3

Another Synthesis of L and D-Oligonucleotides

The oligomers were synthesized on an Expedite™ oligonucleotide synthesizer using a modified 1 μmol RNA cycle, L(D)-ribonucleoside CPG supports, DMT-L(D)-ribonucleoside phosphoramidites and a coupling time of 600 seconds. After deblocking with ethanolic ammonium hydroxide and triethylamine trihydrofluoride, and the oligoribonucleotides were precipitated with n-butanol at −20° C. (23) and desalted on a Nick Sephadex G-50 column. The oligonucleotides were purified by gel-electrophoresis on a 12% polyacrylamide/7M urea denaturing gel. All stock solutions were prepared in nuclease-free water, and were diluted with the appropriate buffers prior to use. The concentrations of RNA oligonucleotides were determined spectrophotometrically, by absorption at 260 nm. The RNA molecules were annealed by heating to 95° C. followed by cooling to room temperature. For the comparison, D-A-site RNA construct was also purchased from Dharmacon and was deprotected using the buffer provided and according to the company's instructions.

EXAMPLE 4

Fluorescence Measurements

5-Carboxytetramethylrhodamine-labeled paromomycin (CRP) and tobramycin (CRT) concentrations were determined spectroscopically at 550 nm using a molar extinction coefficient of 6.00×10 4 M −1 cm −1. Fluorescence anisotropy measurements were performed on a Perkin-Elmer LS-50B luminescence spectrometer equipped with a thermostat accurate to ±0.1° C. as indicated previously (Wang, Y., Hamasaki, K., & Rando, R. R. (1997) Biochemistry 36, 768-779). The tracer solution was excited at 550 nm and monitored at 580 nm. The integration time was 5 s. For every point, 6 measurements were taken, and their average values were used for calculation. Measurements were carried out in a buffer solution containing 150 mM NaCl, 5 mM KCl, 1 mM CaCl$_2$, 1 mM MgCl$_2$, and 20 mM HEPES (pH 7.5). Prior to measurements, RNA constructs were renatured by incubating in binding buffer {150 mM NaCl, 5 mM KCl, 1 mM CaCl$_2$, 1 mM MgCl$_2$, and 20 mM HEPES (pH 7.5)} for 3 minutes at 90° C. followed by slow cooling to 25° C.

EXAMPLE 5

Determination of Dissociation Constants

Equation 1 was used for the determination of the dissociation constant ($K_d$) for the interactions between RNA or ribosome and CRP.

$$A = A_0 + DA\{(RNA)_0 + (CRP)_0 + K_d - (\{(RNA)_0 + (CRP)_0 + K_d\}^2 - 4(RNA)_0(CRP)_0)^{1/2}\}/2$$

where A and $A_0$ are the fluorescence anisotropy of CRP in the presence and absence of RNA, respectively, and DA is the difference between the fluorescence anisotropy of CRP in the presence of an extrapolated infinite concentration of RNA minus the fluorescence anisotropy in the absence of RNA. $(RNA)_0$ and $(CRP)_0$ are the initial concentrations of RNA and CRP, respectively.

Equation 2 is used for the calculation of the $K_D$ values in the competition binding assay.

$$(aminoglycoside)_0 = \{K_D(A_\infty - A)/K_d(A - A_0) + 1\} \{(RNA)_0 - K_d(A - A_0)/(A_\infty - A) - (CRP)_0(A - A_0)/(A_\infty - A)\}$$

where $K_D$ is the dissociation constant between the RNA and the aminoglycosides; $(aminoglycoside)_0$ is the initial concentration of the aminoglycosides; AL is anisotropy of completely bound tracer. Both $K_d$ and $K_D$ were determined by non-linear curve fitting using the equations described above, and are presented as mean values of three independent measurements.

EXAMPLE 6

Preparation of E. coli 70S Ribosomes

The purification of E. coli (E600) 70S ribosomes was carried out according to the published procedure (Lazaro, E., van den Broek, L. A. G. M., Felix, A. S., Ottenheijm, H. C. J., Ballesta, J. P. G. (1991) Biochemistry 30, 9642-9648). E. coli MRE600 were grown for 12 h in 6L of LB medium (10 g trypton, 5 g yeast extract, 5 g NaCl per 1 L, pH 7.0) at 37° C. Crude ribosomes were precipitated from clarified supernatant by 4 h centrifugation at 25,000 rpm in Beckman SW 28 rotor at 4° C. The ribosome pellets were collected in 5 mL of buffer BR1, containing 10 mM HEPES, pH 7.5, 500 mM ammonium acetate, 100 mM magnesium chloride and 2.5 mM DTT. The ribosome suspension was centrifuged for 20 min at 15000 rpm to be clarified. The clarified sample was loaded over two layers of 20% and 40% sucrose in buffer BR1 and centrifuged for 18 hr at 19000 rpm in Beckman SW28 rotor at 4° C. The supernatant was carefully discarded and the purified ribosome pellet was resuspended in buffer BR2 containing 20 mM HEPES pH=7.5, 50 mM ammonium chloride, 12 mM magnesium chloride, and 1 mM DTT. The concentrations of ribosomes were determined by absorbance at 260 nm, assuming 23 pmol/1OD 260, ribosomal suspension was frozen in liquid nitrogen and stored at −80° C.

EXAMPLE 7

Preparation of Yeast 80S Ribosomes

The purification of yeast 80S ribosomes from S. cerevisiae strain YSB 758 was carried out according to the published procedure (Verschoor, A., Warner, J. R., Srivastava, S., Grassucci, R. A., & Frank, J. (1997) Nucl. Acid Res. 26, 655-661). S. cerevisiea YSB 758 were grown for 12 hrs at 30° C. in 2L of YPD medium, containing: 20 g bacto peptone, 20 g glucose, 10 g yeast extract and 0.15 g tryptophan per 1 L, pH 7.0. The cells were lysed by 5-10 cycles of 1 min vigorous shaking with glass beads with a vortex, followed by cooling on ice. Clarified cell extract (about 9 mL total, used in 6 portions in 1.5 mL aliqouts) was carefully loaded on top of 2 mL of a cushion, composed of 10% sucrose and 5% ammonium sulfate dissolved in buffer YR1 (20 mM HEPES pH=7.4, 16 mM magnesium chloride, 100 mM potassium chloride, 5 mM DTT, and 0.5 mM EDTA). The ribosomes were collected by centrifugation in Beckman TL100.3 rotor at 75000 rpm for 3 h. The supernatants were carefully discarded and ribosomes were collected in buffer YR1. The ribosome suspension was clarified by cetrifugation at 14,000 rpm on Eppendorf centrifuge, pellets were discarded. Ribosome concentrations were determined by absorbance at 260 nm, assuming 18 pmol of 80S ribosome particles per 1OD 260. Ribosomes were frozen in liquid nitrogen and stored at −80° C.

EXAMPLE 8

In Vitro Protein Translation

In vitro translation was performed by using PROTEINscript™-PRO (Ambion) kit. This kit is designed for coupled in vitro transcription and translation using a highly active *E. coli* S30 extract, containing 70S ribosomes. Reaction mixtures contained appropriate concentrations of antibiotic (neomycin B, D- and L-neamine). The protein was translated from CAT mRNA, transcribed from control DNA template containing CAT gene under control of the T7 promotor. The product, ~25 kDa chloramphenicol acetyl transferase, was labeled during translation with 1 µCi $^{35}$S methionine (New England Nuclear) per reaction (no cold methionine was added).

Following the translation, the samples were analyzed by electrophoresis on 4-20% SDS mini-gels (Invitrogen) for 1.5 h at 120V. Gels were fixed with 40% methanol/10% acetic acid and exposed to Molecular Dynamics phosphoimager plates, which were read on a Personal FX phosphoimager (Bio-Rad) and quantitated using QuantityOne™ software.

EXAMPLE 9

Antibiotic Activity Disk Assays

*E. coli* (ATCC 25922) and *P. aeruginosa* (ATCC 27853) (BD Bioscience) were inoculated in 3 mL of the medium 2 (U.S. Pharmacopia), containing 6 g peptone, 3 g yeast extract and 1.5 g beef extract per 1 L, pH 6.6, and were grown in a shaker for 6 h at 37° C. until an OD 560=0.6-0.8 was reached. Kanamycin/neomycin resistant *E. coli* was prepared by transformation (electroporation) of wild type (WT) *E. coli* (ATCC 25922) with pMM plasmid, beaiing the gene of aminoglycoside phosphotransferase II (APH(3')IIa), also known as neomycin phosphotransferase II (NPT II, IUBMB Enzyme nomenclature: EC 2.7.1.95) (Wright, G. D. & Thompson, P. R. (1999) Front. Biosci. 4, D9-21). Kanamycin/neomycin resistant *E. coli* was propagated in the same medium 2, supplemented with 30 mg/mL kanamycin.

For the antibiotic disk assay, 50 mL of each bacterial inoculum was mixed with 10 mL of melted agar (1.5% medium 2 agar, BD Bioscience) at 50-55° C. and poured onto 100 mm Petri dishes. Sterile Whatmann 3 MM 5 mm paper disks were soaked with antibiotic solutions and allowed to dry. The disks were positioned evenly on the surface of bacterial-inoculated solid agar and the plates were incubated at 37° C. for 1-2 days. MIC and bactericide index measurements.

EXAMPLE 10

MIC and bactericide Index Measurements

Minimal inhibitory concentrations (MIC) were measured according to the published method (Greenberg, W. A., Priestley, E. S., Sears, P. S., Alper, P. B., Rosenbohm, C., Hendrix, M., Hung, S.-C., & Wong, C.-H. (1999) J. Am. Chem. Soc. 121, 6527-6541). *E. coli* (ATCC 25922) (both wild type and pMM-transformed) and *P. aeruginosa* (ATCC 27853) were grown in medium 2 to an optical density OD 600 of 0.6-0.8. The inoculi were diluted to OD 600 ~0.1 in medium 2 and 1 mL of the culture was placed in 13 mL test tubes. The desired concentrations of antibiotic were added from stock solutions. The samples were incubated at 37° C. for 3-5 h when the control culture had an OD 600 of 1.2-1.5. The absorbance at 600 nm of each sample was read and MIC was taken as the lowest antibiotic concentration inhibiting bacterial growth by greater than 90%.

The bactericidal activity of each antibiotic was investigated at concentrations of 0.5-4×MIC in medium *E. coli* (ATCC 25922) inoculum was added to 0.5 mL medium 2 to OD 600 ~0.1 together with different antibiotic concentrations. The samples were incubated at 37° C. for 3 hrs, and the bacteria were collected by centrifugation. The bacterial pellets were washed with 0.5 mL of medium 2 and were plated on 1.5% medium 2 agar in 100 mm Petri dishes. The plates were incubated for 1-2 days at 37° C. and mean log 10 change in viable count was calculated and plotted vs drug concentration.

EXAMPLE 11

RNA Footprinting

For the footprinting experiments, the L-A-site RNA construct was synthesized with a 3-D-adenosine ($A_3$) tail at 5' end (FIG. 11). The RNA was purified by gel-electrophoresis on a 12% polyacrylainide/7M urea gel as described above. The purified D and L-RNA were radioactively labeled at 5' end with 1 µL of $^{32}$P γ-ATP (6000 Ci/nmmol, New England Nuclear) per 1 nmol of RNA using T4 polynucleotide kinase (Ambion) in a buffer containing 70 mM Tris-HCl, pH 7.5, 10 mM $MgCl_2$, and 5 mM DTT. The labeled D- and L-RNA was successively extracted with water-saturated phenol, phenol/chloroform (1:1), and chloroform, and precipitated from 75% ethanol. All RNA samples were annealed by heating them to 95° C. for 3 nmin, followed by cooling to room temperature in a 10 mM HEPES buffer (pH 7.0).

EXAMPLE 12

Lead (II) Acetate Footprinting

In a typical experiment, 10 µL of 10 mM HEPES buffer, pH 7.0, containing 50 mM KCl, was incubated with 50-100 ng of 5'-$^{32}$P-labeled D- or L-RNA oligonucleotide (approximately 0.25-0.5 µM) in the presence of 0.5 µg tRNA and varying concentrations of D-, L-neamine or neomycin B at room temperature for 5 min. Cleavage reactions were initiated by addition of $Pb(OAc)_2$ to final concentrations of 0.1 mM. After 20 min incubation at room temperature, 10 µL of formamide/bromphenol blue/xylene cyanol loading buffer, containing 10 mM EDTA, were added to the samples. The samples were heated to 90° C. for 2 min and were resolved by electrophoresis on a 40 cm×0.75 mm 20% polyacrylamide denaturing gel (7M urea) for 3.5 h at 50 W constant power. The results were visualized by exposing the wet gels to Molecular Dynamics phosphoimager plates, which were read on a Personal FX phosphoimager (Bio-Rad) and quantitated using QuantityOne™ software.

EXAMPLE 13

DMS Footprinting

In a typical experiment, 10 µL of 10 mM HEPES buffer, pH 7.0, containing 50 mM KCl, were incubated with 100 ng of 5'-$^{32}$P-labeled D- or L-RNA oligonucleotide in the presence of of 0.5 µg tRNA and varying concentrations of D-, L-neamine or neomycin B at room temperature for 5 min.

One μL of neat dimethyl sulfate (DMS, Sigma) was added to the samples. After 5 minutes incubation at room temperature, the RNA was precipitated by the addition of 1 μL 3M sodium acetate and 32 μL of ice-cold ethanol (75% final ethanol concentration) followed by incubation for 1-2 hrs at −20° C. The RNA pelleted by centrifugation at 14000 rpm for 20 min. The pellets were washed with 75% ethanol, dried and dissolved in 10 μL of 1M Tris HCl, pH 7.3. 10 μL of freshly prepared 0.2 M sodium borohydride (Sigma) solution was added to the samples, and further incubation was allowed for 30 minutes on ice in the dark. Following the sodium borohydride treatment, the samples were precipitated from 75% ethanol as described above. After the pellets were washed and dried, they were dissolved in 20 μL of fresh aniline acetate solution, prepared by addition to 210 μL of glacial acetic acid, 90 μL of water and 30 μL of freshly distilled aniline. The RNA samples were incubated at 60° C. for 20 min, and the reaction was stopped by freezing on dry ice. The samples were lyophilized, the pellets were washed twice with ethanol, dissolved in 20 μL water and lyophilized again. The samples then were dissolved in 10 μL of formamide/bromphenol blue\xylene cyanol loading buffer and gel-electrophoretic analysis was performed as described above.

What is claimed is:

1. An aminoglycoside compound comprising a plurality of azasugar residues wherein at least one azasugar residue is a diasteroemer or enantiomer of D-neamine or a derivative thereof.

2. The aminoglycoside compound of claim 1, wherein substantially all of the azasugar residues of the aminoglycoside compound are L-azasugar residues which are diastereomers or enantiomers of D-neamine or a derivative thereof.

3. The aminoglycoside compound of claim 1, wherein the aminoglycoside compound is an L-aminoglycoside compound or a diastereomer of an L-aminoglycoside differing by stereochemical identity at from 1 to 3 stereocenters from the L-aminoglycoside compound which is a mirror image of a D-aminoglycoside capable of inhibiting bacteria growth.

4. The aminoglycoside compound of claim 1, wherein the aminoglycoside is a L-neamine or an L-neamine derivative which optionally has one or more D- or L-sugar or D- or L-azasugar residues coupled to the L-neamine core and one or more of the hydroxyl or amino groups of the aminoglycoside are optionally substituted.

5. The aminoglycoside compound of claim 1, which is L-neamine or a L-neamine derivative selected from the group consisting of L-neomycin, L-paromomycin, L-kanamycin, and L-tobramycin.

6. The aminoglycoside compound of claim 1 wherein the L-neamine or L-neamine derivative is capable of inhibiting bacterial growth.

7. The aminoglycoside compound of claim 1, wherein the aminoglycoside has antibiotic activity against strains of bacteria or yeast which are resistant to D-aminoglycoside antibiotics.

8. An L-aminoglycoside compound of the formula:

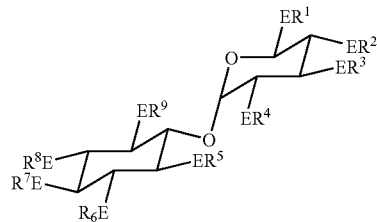

wherein

E is independently selected at each occurrence of E in the formula from the group consisting of O, NH, and N—$C_{1-6}$alkyl;

$R^1$, $R^2$, $R^3$, $R^4$, $R^5$, $R^6$, $R^7$, $R^8$, and $R^9$ are independently selected at each occurrence from the groups consisting of hydrogen, $C_{1-6}$alkyl, $C_{1-6}$alkanoyl, monosaccharides, disaccharides, mono-azasaccharides, and di-azasaccharides, where each saccharide or azasaccharide residue is either a D-saccharide or an L-saccharide; wherein at least one E is NH or N—$C_{1-6}$alkyl.

9. An aminoglycoside compound according to the formula:

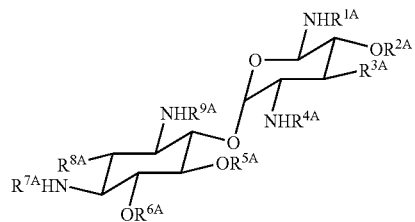

wherein $R^{1A}$, $R^{2A}$, $R^{4A}$, $R^{5A}$, $R^{6A}$, $R^{7A}$, and $R^{9A}$ are independently selected at each occurrence from the groups consisting of hydrogen, alkyl, alkanoyl, monosaccharides, disaccharides, mono-azasaccharides, and di-azasaccharides, where each saccharide or azasaccharide residue is either a D-saccharide or an L-saccharide; and $R^{3A}$ and $R^{8A}$ are independently selected at each occurrence from the groups consisting of hydrogen, hydroxy, amino, $C_{1-6}$alkoxy, amino, mono and di$C_{1-6}$alkylamino, carboxamide, monosaccharides, disaccharides, mono-azasaccharides, and di-azasaccharides, where each saccharide or azasaccharide residue is either a D-saccharide or an L-saccharide.

10. The aminoglycoside compound of claim 1, wherein the compound is not susceptible to loss of antibiotic activity through metabolic processes.

11. A pharmaceutical composition comprising a compound of any one of claims 1 through 10 and a pharmaceutically acceptable carrier.

* * * * *